(12) United States Patent
Kornerup et al.

(10) Patent No.: US 8,221,355 B2
(45) Date of Patent: Jul. 17, 2012

(54) INJECTION DEVICE FOR INFUSION SET

(75) Inventors: Grete Kornerup, Vipperød (DK); Lasse W. Mogensen, Søborg (DK); Magnus W. Göransson, Malmö (DK)

(73) Assignee: Unomedical A/S, Birkeroed (DK)

( * ) Notice: Subject to any disclaimer, the term of this patent is extended or adjusted under 35 U.S.C. 154(b) by 834 days.

(21) Appl. No.: 10/594,043

(22) PCT Filed: Mar. 21, 2005

(86) PCT No.: PCT/DK2005/000190
§ 371 (c)(1),
(2), (4) Date: Aug. 21, 2007

(87) PCT Pub. No.: WO2005/092411
PCT Pub. Date: Oct. 6, 2005

(65) Prior Publication Data
US 2008/0039794 A1 Feb. 14, 2008

Related U.S. Application Data

(63) Continuation of application No. PCT/DK2005/000190, filed on Mar. 21, 2005.

(60) Provisional application No. 60/556,863, filed on Mar. 26, 2004.

(30) Foreign Application Priority Data

Mar. 26, 2004 (DK) ................................ 2004 00493

(51) Int. Cl.
*A61M 5/158* (2006.01)
*A61M 5/14* (2006.01)

(52) U.S. Cl. ..................... 604/136; 604/180.1; 604/506; 604/164.04; 604/164.12

(58) Field of Classification Search ................... 604/19, 604/21, 48, 502, 506, 93.01, 164.01, 164.04, 604/164.07, 164.11–164.12, 165.01, 165.03, 604/170.01, 170.02, 174–175, 179, 181, 604/200–201, 264, 272, 890.1, 539, 70.01, 604/136; 600/564, 566–567
See application file for complete search history.

(56) References Cited

U.S. PATENT DOCUMENTS 643,544 A 2/1900 Simmons
(Continued)

FOREIGN PATENT DOCUMENTS

DE 893 296 12/1953
DE 1 053 541 3/1959
DE 26 20 009 A1 12/1977
DE 28 03 509 A1 8/1979
DE 37 22 893 C1 6/1988
(Continued)

OTHER PUBLICATIONS

International Search Report dated Jun. 10, 2005 for International Application No. PCT/DK2005/000190.
(Continued)

*Primary Examiner* — Quynh-Nhu H Vu
(74) *Attorney, Agent, or Firm* — Brinks Hofer Gilson & Lione

(57) ABSTRACT

The invention relates to an injector device for an infusion set for intermittent or continuous administration of a therapeutical substance, such as insulin. The injector device for the subcutaneous introduction of the cannula of an infusion part into the skin of a patient comprises a housing, a back, longitudinally extending guiding means, a member which is longitudinally slidable within the housing, an insertion needle for insertion of the cannula, a spring located between the back of the housing and the longitudinally slidable member, locking means for maintaining the spring in a compressed state and release means for disengaging the locking means. The device further comprises a pivoting member which can be swung from a position in which the pivoting member allows for insertion of the needle into a position in which it embraces the needle.

9 Claims, 27 Drawing Sheets

U.S. PATENT DOCUMENTS

| | | |
|---|---|---|
| 1,592,462 A | 7/1926 | MacGregor |
| 1,838,825 A | 1/1929 | Goldstein |
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapata |
| 2,952,420 A | 9/1960 | Von Hoorn |
| 2,972,779 A | 2/1961 | Cowley |
| 3,055,361 A | 9/1962 | Ballard |
| 3,059,802 A | 10/1962 | Mitchell |
| 3,074,541 A | 1/1963 | Roehr |
| 3,107,785 A | 10/1963 | Roehr |
| 3,154,080 A | 10/1964 | Rowan et al. |
| 3,221,739 A | 12/1965 | Rosenthal |
| 3,221,740 A | 12/1965 | Rosenthal |
| 3,306,291 A | 2/1967 | Burke |
| 3,317,166 A | 5/1967 | Janssen |
| 3,485,352 A | 12/1969 | Pilger |
| 3,509,879 A | 5/1970 | Bathish et al. |
| 3,519,158 A | 7/1970 | Anderson |
| 3,545,286 A | 12/1970 | Stenstrom |
| 3,547,119 A | 12/1970 | Hall et al. |
| 3,610,240 A | 10/1971 | Harautuneian |
| 3,648,999 A | 3/1972 | Bauer |
| 3,670,727 A | 6/1972 | Reiterman |
| 3,783,996 A | 1/1974 | Gerard et al. |
| 3,788,374 A | 1/1974 | Saijo |
| 3,810,469 A | 5/1974 | Hurschman |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,893,448 A | 7/1975 | Brantigan |
| 3,937,219 A | 2/1976 | Karakashian |
| 3,942,528 A | 3/1976 | Loeser |
| 3,986,507 A | 10/1976 | Watt |
| 3,986,508 A | 10/1976 | Barrington |
| 3,995,518 A | 12/1976 | Spiroff |
| 4,014,328 A | 3/1977 | Cluff et al. |
| 4,022,205 A | 5/1977 | Tenczar |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,306,705 A | 12/1981 | Svensson |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,365,630 A | 12/1982 | McFarlane |
| 4,378,015 A | 3/1983 | Wardlaw |
| 4,400,861 A | 8/1983 | Parker |
| 4,406,042 A | 9/1983 | McPhee |
| 4,415,393 A | 11/1983 | Grimes |
| 4,417,886 A | 11/1983 | Frankhouser et al. |
| 4,458,344 A | 7/1984 | Coogler |
| 4,464,178 A | 8/1984 | Dalton |
| 4,472,024 A | 9/1984 | Konomura et al. |
| 4,473,369 A | 9/1984 | Lueders et al. |
| 4,484,910 A | 11/1984 | Sarnoff et al. |
| 4,500,312 A | 2/1985 | McFarlane |
| 4,517,971 A | 5/1985 | Sorbonned |
| 4,525,157 A | 6/1985 | Vaillancourt |
| 4,530,695 A | 7/1985 | Phillips et al. |
| 4,531,686 A | 7/1985 | Shaw |
| 4,531,937 A | 7/1985 | Yates |
| 4,563,177 A | 1/1986 | Kamen |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,617,019 A | 10/1986 | Fecht |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,727,999 A | 3/1988 | Gach |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,077,872 A | 1/1992 | Guthammar |
| 5,083,757 A | 1/1992 | Barsky |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,129,884 A | 7/1992 | Dysarz |
| 5,134,593 A | 7/1992 | Logan et al. |
| 5,134,594 A | 7/1992 | Woo |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,314 A | 2/1993 | Peters |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |

| Patent No. | Date | Inventor |
|---|---|---|
| 5,265,822 A | 11/1993 | Shober, Jr. et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| 5,439,473 A * | 8/1995 | Jorgensen ..................... 606/182 |
| D362,718 S | 9/1995 | Deily et al. |
| 5,449,349 A | 9/1995 | Sallee et al. |
| 5,451,210 A | 9/1995 | Kramer et al. |
| 5,487,506 A | 1/1996 | Drummond et al. |
| 5,490,841 A | 2/1996 | Landis |
| 5,492,313 A | 2/1996 | Pan et al. |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,519,167 A | 5/1996 | Kunimoto et al. |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A * | 12/1996 | Livingston et al. ............ 604/177 |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A * | 5/1997 | Morita .......................... 606/182 |
| 5,643,214 A | 7/1997 | Marshall |
| 5,643,216 A | 7/1997 | White |
| 5,643,220 A | 7/1997 | Cosme |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,516 A | 1/1998 | Peterson et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| D402,538 S | 12/1998 | Wagter et al. |
| 5,843,001 A | 12/1998 | Goldenberg |
| 5,848,990 A | 12/1998 | Cirelli et al. |
| 5,851,197 A * | 12/1998 | Marano et al. ................. 604/135 |
| 5,858,001 A * | 1/1999 | Tsals et al. ..................... 604/135 |
| 5,865,806 A | 2/1999 | Howell |
| 5,873,540 A | 2/1999 | Hardin |
| 5,899,886 A | 5/1999 | Cosme |
| 5,911,705 A | 6/1999 | Howell |
| 5,913,846 A | 6/1999 | Szabo |
| 5,915,640 A | 6/1999 | Wagter et al. |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,947,931 A | 9/1999 | Bierman |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,968,011 A | 10/1999 | Larsen et al. |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| 5,992,787 A | 11/1999 | Burke |
| 417,733 A | 12/1999 | Howell et al. |
| 6,017,328 A | 1/2000 | Fischell et al. |
| 6,017,598 A | 1/2000 | Kreischer et al. |
| 421,119 A | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |

| | | | | | | |
|---|---|---|---|---|---|---|
| 6,355,021 B1 | 3/2002 | Nielsen et al. | | 7,147,623 B2 | 12/2006 | Mathiasen |
| 6,379,335 B1 | 4/2002 | Rigon et al. | | 7,186,236 B2 | 3/2007 | Gibson et al. |
| D456,692 S | 5/2002 | Epstein | | 7,211,068 B2 | 5/2007 | Douglas |
| 6,387,076 B1 | 5/2002 | Van Landuyt | | 7,214,207 B2 | 5/2007 | Lynch et al. |
| 6,387,078 B1 | 5/2002 | Gillespie, III | | 7,214,215 B2 | 5/2007 | Heinzerling et al. |
| 6,405,876 B1 | 6/2002 | Seshimoto et al. | | 7,250,037 B2 | 7/2007 | Shermer et al. |
| 6,440,096 B1 | 8/2002 | Lastovich et al. | | 7,258,680 B2 | 8/2007 | Mogensen et al. |
| 6,447,482 B1 | 9/2002 | Rønborg et al. | | D554,253 S | 10/2007 | Kornerup |
| 6,450,992 B1 | 9/2002 | Cassidy, Jr. | | 7,303,543 B1 | 12/2007 | Maule et al. |
| 6,488,663 B1 | 12/2002 | Steg | | 7,309,326 B2 | 12/2007 | Fangrow, Jr. |
| 6,503,222 B2 | 1/2003 | Lo | | 7,318,816 B2 * | 1/2008 | Bobroff et al. ............... 604/136 |
| 6,517,517 B1 | 2/2003 | Farrugia et al. | | 7,407,491 B2 | 8/2008 | Fangrow, Jr. |
| 6,520,938 B1 | 2/2003 | Funderburk et al. | | 7,407,493 B2 | 8/2008 | Cane' |
| D472,316 S | 3/2003 | Douglas et al. | | 7,431,876 B2 | 10/2008 | Mejlhede et al. |
| D472,630 S | 4/2003 | Douglas et al. | | 7,569,262 B2 | 8/2009 | Szabo et al. |
| 6,572,586 B1 | 6/2003 | Wojcik | | 7,648,494 B2 | 1/2010 | Kornerup et al. |
| 6,579,267 B2 | 6/2003 | Lynch et al. | | 7,766,867 B2 | 8/2010 | Lynch et al. |
| 6,582,397 B2 | 6/2003 | Alesi et al. | | 2001/0004970 A1 | 6/2001 | Hollister et al. |
| 6,595,962 B1 | 7/2003 | Perthu | | 2001/0016714 A1 | 8/2001 | Bell et al. |
| 6,607,509 B2 | 8/2003 | Bobroff et al. | | 2001/0021827 A1 | 9/2001 | Ferguson et al. |
| 6,607,511 B2 | 8/2003 | Halseth et al. | | 2001/0039387 A1 | 11/2001 | Rutynowski et al. |
| 6,613,064 B2 | 9/2003 | Rutynowski et al. | | 2001/0039401 A1 | 11/2001 | Ferguson et al. |
| 6,620,133 B1 | 9/2003 | Steck | | 2001/0041875 A1 | 11/2001 | Higuchi et al. |
| 6,620,136 B1 | 9/2003 | Pressly, Sr. et al. | | 2001/0049496 A1 | 12/2001 | Kirchhofer |
| 6,620,140 B1 | 9/2003 | Metzger | | 2001/0053889 A1 | 12/2001 | Marggi |
| 6,629,949 B1 | 10/2003 | Douglas | | 2001/0056284 A1 | 12/2001 | Purcell et al. |
| 6,645,181 B1 | 11/2003 | Lavi et al. | | 2002/0022798 A1 | 2/2002 | Connelly |
| 6,645,182 B1 | 11/2003 | Szabo | | 2002/0022855 A1 | 2/2002 | Bobroff et al. |
| 6,659,982 B2 | 12/2003 | Douglas et al. | | 2002/0026152 A1 | 2/2002 | Bierman |
| 6,685,674 B2 | 2/2004 | Douglas et al. | | 2002/0068904 A1 | 6/2002 | Bierman et al. |
| 6,699,218 B2 | 3/2004 | Flaherty et al. | | 2002/0072720 A1 | 6/2002 | Hague et al. |
| 6,702,779 B2 | 3/2004 | Connelly et al. | | 2002/0074345 A1 | 6/2002 | Schneider et al. |
| 6,726,649 B2 | 4/2004 | Swenson et al. | | 2002/0077599 A1 | 6/2002 | Wojcik |
| 6,736,797 B1 | 5/2004 | Larsen et al. | | 2002/0082543 A1 | 6/2002 | Park et al. |
| 6,749,587 B2 | 6/2004 | Flaherty | | 2002/0107489 A1 | 8/2002 | Lee |
| 6,749,589 B1 | 6/2004 | Douglas et al. | | 2002/0111581 A1 | 8/2002 | Sasso |
| 6,755,805 B1 | 6/2004 | Reid | | 2002/0145073 A1 | 10/2002 | Swanson |
| 6,776,775 B1 | 8/2004 | Mohammad | | 2002/0156424 A1 | 10/2002 | Suzuki et al. |
| 6,790,199 M1 | 9/2004 | Gianakos | | 2002/0156427 A1 | 10/2002 | Suzuki et al. |
| 6,805,686 B1 | 10/2004 | Fathallah et al. | | 2002/0161322 A1 | 10/2002 | Utterberg et al. |
| 6,808,506 B2 | 10/2004 | Lastovich et al. | | 2002/0161332 A1 | 10/2002 | Ramey |
| 6,811,545 B2 | 11/2004 | Vaillancourt | | 2002/0161386 A1 | 10/2002 | Halseth et al. |
| 6,814,720 B2 | 11/2004 | Olsen et al. | | 2002/0165493 A1 | 11/2002 | Bierman |
| 6,824,530 B2 * | 11/2004 | Wagner et al. ............... 604/162 | | 2002/0169419 A1 | 11/2002 | Steg |
| 6,824,531 B1 | 11/2004 | Zecha, Jr. et al. | | 2002/0173748 A1 | 11/2002 | McConnell et al. |
| 6,830,562 B2 | 12/2004 | Mogensen et al. | | 2002/0173769 A1 | 11/2002 | Gray et al. |
| 6,837,877 B2 | 1/2005 | Zurcher | | 2002/0183688 A1 | 12/2002 | Lastovich et al. |
| 6,837,878 B2 | 1/2005 | Smutney et al. | | 2002/0189688 A1 | 12/2002 | Roorda |
| 6,840,922 B2 | 1/2005 | Nielsen et al. | | 2002/0193737 A1 | 12/2002 | Popovsky |
| 6,880,701 B2 | 4/2005 | Bergeron et al. | | 2002/0193744 A1 | 12/2002 | Alesi et al. |
| 6,916,017 B2 | 7/2005 | Noe | | 2003/0014018 A1 | 1/2003 | Giambattista et al. |
| 6,923,791 B2 | 8/2005 | Douglas | | 2003/0060781 A1 | 3/2003 | Mogensen et al. |
| 6,926,694 B2 | 8/2005 | Marano-Ford et al. | | 2003/0069548 A1 | 4/2003 | Connelly et al. |
| 6,939,331 B2 | 9/2005 | Ohshima | | 2003/0088238 A1 | 5/2003 | Poulsen et al. |
| 6,949,084 B2 | 9/2005 | Marggi et al. | | 2003/0105430 A1 | 6/2003 | Lavi et al. |
| 6,959,812 B2 | 11/2005 | Reif et al. | | 2003/0109829 A1 | 6/2003 | Mogensen et al. |
| 6,960,193 B2 | 11/2005 | Rosenberg | | 2003/0125669 A1 | 7/2003 | Safabash et al. |
| 6,979,316 B1 | 12/2005 | Rubin et al. | | 2003/0125678 A1 | 7/2003 | Swenson et al. |
| 6,991,619 B2 | 1/2006 | Marano-Ford et al. | | 2003/0130619 A1 | 7/2003 | Safabash et al. |
| 6,991,620 B2 | 1/2006 | Marano-Ford et al. | | 2003/0139704 A1 | 7/2003 | Lin |
| 6,994,213 B2 | 2/2006 | Giard et al. | | 2003/0158520 A1 | 8/2003 | Safabash et al. |
| 6,997,907 B2 | 2/2006 | Safabash et al. | | 2003/0176843 A1 | 9/2003 | Wilkenson |
| 7,014,625 B2 | 3/2006 | Bengtsson | | 2003/0176852 A1 | 9/2003 | Lynch et al. |
| 7,018,344 B2 | 3/2006 | Bressler et al. | | 2003/0181863 A1 | 9/2003 | Davis et al. |
| 7,022,108 B2 | 4/2006 | Marano-Ford et al. | | 2003/0181868 A1 | 9/2003 | Swenson |
| 7,047,070 B2 | 5/2006 | Wilkenson et al. | | 2003/0181873 A1 | 9/2003 | Swenson |
| 7,052,483 B2 | 5/2006 | Wojcik | | 2003/0181874 A1 | 9/2003 | Bressler et al. |
| 7,055,713 B2 | 6/2006 | Rea et al. | | 2003/0187394 A1 | 10/2003 | Wilkinson et al. |
| 7,056,302 B2 | 6/2006 | Douglas | | 2003/0187395 A1 | 10/2003 | Wilkinson et al. |
| 7,070,580 B2 | 7/2006 | Nielsen | | 2003/0199823 A1 | 10/2003 | Bobroff et al. |
| 7,074,208 B2 | 7/2006 | Pajunk et al. | | 2003/0216686 A1 | 11/2003 | Lynch et al. |
| D526,409 S | 8/2006 | Nielsen et al. | | 2003/0220610 A1 | 11/2003 | Lastovich et al. |
| 7,083,592 B2 | 8/2006 | Lastovich et al. | | 2003/0225373 A1 | 12/2003 | Bobroff et al. |
| 7,083,597 B2 | 8/2006 | Lynch et al. | | 2003/0225374 A1 | 12/2003 | Mathiasen |
| 7,097,631 B2 | 8/2006 | Trautman et al. | | 2003/0229308 A1 | 12/2003 | Tsals et al. |
| 7,109,878 B2 | 9/2006 | Mann et al. | | 2003/0229316 A1 | 12/2003 | Hwang et al. |
| 7,115,108 B2 | 10/2006 | Wilkenson et al. | | 2004/0002682 A1 | 1/2004 | Kovelman et al. |
| 7,115,112 B2 | 10/2006 | Mogensen et al. | | 2004/0006316 A1 | 1/2004 | Patton |
| 7,141,023 B2 | 11/2006 | Diermann et al. | | 2004/0026840 A1 | 2/2004 | Eckel et al. |

| | | | |
|---|---|---|---|
| 2004/0044306 A1 | 3/2004 | Lynch et al. | |
| 2004/0049159 A1 | 3/2004 | Barrus et al. | |
| 2004/0059316 A1 | 3/2004 | Smedegaard | |
| 2004/0068231 A1 | 4/2004 | Blondeau | |
| 2004/0069044 A1 | 4/2004 | Lavi et al. | |
| 2004/0087913 A1 | 5/2004 | Rogers et al. | |
| 2004/0092865 A1 | 5/2004 | Flaherty et al. | |
| 2004/0092875 A1 | 5/2004 | Kochamba | |
| 2004/0111068 A1 | 6/2004 | Swenson | |
| 2004/0112781 A1 | 6/2004 | Hofverberg et al. | |
| 2004/0116865 A1 | 6/2004 | Bengtsson | |
| 2004/0133164 A1 | 7/2004 | Funderburk et al. | |
| 2004/0138612 A1 | 7/2004 | Shermer et al. | |
| 2004/0138620 A1 | 7/2004 | Douglas et al. | |
| 2004/0143216 A1 | 7/2004 | Douglas et al. | |
| 2004/0143218 A1 | 7/2004 | Das | |
| 2004/0158202 A1 | 8/2004 | Jensen | |
| 2004/0158207 A1* | 8/2004 | Hunn et al. | 604/164.01 |
| 2004/0162518 A1 | 8/2004 | Connelly et al. | |
| 2004/0171989 A1 | 9/2004 | Horner et al. | |
| 2004/0178098 A1 | 9/2004 | Swenson et al. | |
| 2004/0186446 A1 | 9/2004 | Ohshima | |
| 2004/0193143 A1 | 9/2004 | Sauer | |
| 2004/0199123 A1 | 10/2004 | Nielsen | |
| 2004/0204673 A1 | 10/2004 | Flaherty et al. | |
| 2004/0204687 A1 | 10/2004 | Mogensen et al. | |
| 2004/0204690 A1 | 10/2004 | Yashiro et al. | |
| 2004/0215151 A1 | 10/2004 | Marshall et al. | |
| 2004/0220528 A1 | 11/2004 | Garcia, Jr. | |
| 2004/0236284 A1 | 11/2004 | Hoste et al. | |
| 2004/0238392 A1 | 12/2004 | Peterson et al. | |
| 2004/0243065 A1 | 12/2004 | McConnell et al. | |
| 2004/0254433 A1 | 12/2004 | Bandis et al. | |
| 2004/0260235 A1 | 12/2004 | Douglas | |
| 2004/0260250 A1* | 12/2004 | Harris et al. | 604/263 |
| 2005/0035014 A1 | 2/2005 | Cane | |
| 2005/0038378 A1 | 2/2005 | Lastovich et al. | |
| 2005/0043687 A1 | 2/2005 | Mogensen et al. | |
| 2005/0049571 A1 | 3/2005 | Lastovich et al. | |
| 2005/0065466 A1 | 3/2005 | Vedrine | |
| 2005/0065472 A1 | 3/2005 | Cindrich et al. | |
| 2005/0075606 A1 | 4/2005 | Botich et al. | |
| 2005/0101910 A1 | 5/2005 | Bowman et al. | |
| 2005/0101912 A1 | 5/2005 | Faust et al. | |
| 2005/0101932 A1 | 5/2005 | Cote et al. | |
| 2005/0101933 A1 | 5/2005 | Marrs et al. | |
| 2005/0107743 A1 | 5/2005 | Fangrow, Jr. | |
| 2005/0113761 A1 | 5/2005 | Faust et al. | |
| 2005/0119611 A1 | 6/2005 | Marano-Ford et al. | |
| 2005/0119619 A1 | 6/2005 | Haining | |
| 2005/0119637 A1 | 6/2005 | Lundgren et al. | |
| 2005/0124936 A1 | 6/2005 | Mogensen et al. | |
| 2005/0131347 A1 | 6/2005 | Marano-Ford et al. | |
| 2005/0159709 A1 | 7/2005 | Wilkinson | |
| 2005/0159714 A1 | 7/2005 | Gibson | |
| 2005/0165382 A1 | 7/2005 | Fulford | |
| 2005/0192560 A1 | 9/2005 | Walls et al. | |
| 2005/0203461 A1 | 9/2005 | Flaherty et al. | |
| 2005/0215979 A1 | 9/2005 | Konerup et al. | |
| 2005/0240154 A1 | 10/2005 | Mogensen et al. | |
| 2005/0251098 A1 | 11/2005 | Wyss et al. | |
| 2005/0256456 A1 | 11/2005 | Marano-Ford et al. | |
| 2005/0261629 A1 | 11/2005 | Marano-Ford et al. | |
| 2005/0277892 A1 | 12/2005 | Chen | |
| 2005/0283114 A1 | 12/2005 | Bresina et al. | |
| 2006/0015063 A1 | 1/2006 | Butikofer et al. | |
| 2006/0015076 A1 | 1/2006 | Heinzerling et al. | |
| 2006/0030815 A1 | 2/2006 | Csincsura et al. | |
| 2006/0036214 A1 | 2/2006 | Mogensen et al. | |
| 2006/0041224 A1 | 2/2006 | Jensen | |
| 2006/0069351 A9* | 3/2006 | Safabash et al. | 604/136 |
| 2006/0069382 A1 | 3/2006 | Pedersen | |
| 2006/0069383 A1 | 3/2006 | Bogaerts et al. | |
| 2006/0095003 A1 | 5/2006 | Marano-Ford et al. | |
| 2006/0095014 A1 | 5/2006 | Ethelfeld | |
| 2006/0106346 A1 | 5/2006 | Sullivan et al. | |
| 2006/0129123 A1 | 6/2006 | Wojcik | |
| 2006/0135908 A1 | 6/2006 | Liniger et al. | |
| 2006/0135913 A1 | 6/2006 | Ethelfeld | |
| 2006/0142698 A1 | 6/2006 | Ethelfeld | |
| 2006/0161108 A1 | 7/2006 | Mogensen et al. | |
| 2006/0173410 A1 | 8/2006 | Moberg et al. | |
| 2006/0173413 A1 | 8/2006 | Fan | |
| 2006/0184104 A1 | 8/2006 | Cheney, II et al. | |
| 2006/0184140 A1 | 8/2006 | Okiyama | |
| 2006/0200073 A1 | 9/2006 | Radmer et al. | |
| 2006/0241551 A1 | 10/2006 | Lynch et al. | |
| 2006/0247553 A1 | 11/2006 | Diermann et al. | |
| 2006/0247574 A1 | 11/2006 | Maule et al. | |
| 2006/0253085 A1 | 11/2006 | Geismar et al. | |
| 2006/0253086 A1 | 11/2006 | Moberg et al. | |
| 2006/0264835 A1 | 11/2006 | Nielsen et al. | |
| 2006/0264890 A1 | 11/2006 | Moberg et al. | |
| 2007/0005017 A1 | 1/2007 | Alchas et al. | |
| 2007/0016129 A1 | 1/2007 | Liniger et al. | |
| 2007/0016159 A1 | 1/2007 | Sparholt et al. | |
| 2007/0021729 A1 | 1/2007 | Mogensen et al. | |
| 2007/0049865 A1 | 3/2007 | Radmer et al. | |
| 2007/0049870 A1 | 3/2007 | Gray et al. | |
| 2007/0066955 A1 | 3/2007 | Sparholt et al. | |
| 2007/0088271 A1 | 4/2007 | Richards | |
| 2007/0093754 A1 | 4/2007 | Mogensen et al. | |
| 2007/0104596 A1 | 5/2007 | Preuthun et al. | |
| 2007/0112301 A1 | 5/2007 | Preuthun et al. | |
| 2007/0112303 A1 | 5/2007 | Liniger | |
| 2007/0129688 A1 | 6/2007 | Scheider et al. | |
| 2007/0173767 A1 | 7/2007 | Lynch et al. | |
| 2007/0179444 A1 | 8/2007 | Causey et al. | |
| 2007/0185441 A1 | 8/2007 | Fangrow, Jr. | |
| 2007/0191772 A1 | 8/2007 | Wojcik | |
| 2007/0191773 A1 | 8/2007 | Wojcik | |
| 2007/0203454 A1 | 8/2007 | Shermer et al. | |
| 2007/0213673 A1 | 9/2007 | Douglas | |
| 2007/0244448 A1 | 10/2007 | Lastovich et al. | |
| 2008/0312601 A1 | 12/2008 | Cane' | |
| 2010/0004597 A1 | 1/2010 | Gyrn et al. | |
| 2010/0137829 A1 | 6/2010 | Nielsen et al. | |
| 2010/0228226 A1 | 9/2010 | Nielsen | |

FOREIGN PATENT DOCUMENTS

| | | |
|---|---|---|
| DE | 4 342 329 A1 | 6/1994 |
| DE | 196 31 921 A1 | 3/1997 |
| DE | 196 10 692 A1 | 9/1997 |
| DE | 298 18 311 U1 | 3/1999 |
| DE | 299 05 072 U1 | 9/1999 |
| DE | 38 23 447 C3 | 10/1999 |
| DE | 19847143 A1 | 1/2000 |
| DE | 299 21 406 U1 | 11/2001 |
| DE | 101 06 074 A1 | 6/2002 |
| DE | 101 17 285 A1 | 11/2002 |
| DE | 203 20 207 U1 | 11/2004 |
| DK | 37 22 893 C1 | 6/1988 |
| DK | 38 23 447 C3 | 2/1996 |
| DK | 196 10 692 A1 | 9/1997 |
| DK | 100 49 001 A1 | 4/2002 |
| EP | 0117632 B1 | 9/1984 |
| EP | 0 188 014 B1 | 10/1985 |
| EP | 0 239 244 B1 | 2/1987 |
| EP | 0272530 A2 | 6/1988 |
| EP | 0 298 521 B1 | 9/1990 |
| EP | 0451040 A1 | 10/1991 |
| EP | 0 184 231 B1 | 1/1992 |
| EP | 0 475 857 A1 | 3/1992 |
| EP | 0 544 837 B1 | 6/1993 |
| EP | 0 633 039 A1 | 7/1994 |
| EP | 0615768 A2 | 9/1994 |
| EP | 0 651 662 B1 | 5/1995 |
| EP | 0652027 A1 | 5/1995 |
| EP | 0 657 184 A1 | 6/1995 |
| EP | 0 714 631 B1 | 6/1996 |
| EP | 744 183 A2 | 11/1996 |
| EP | 0 747 006 A1 | 12/1996 |
| EP | 0799626 A1 | 10/1997 |
| EP | 0 688 232 B1 | 12/1998 |
| EP | 0 884 108 A1 | 12/1998 |
| EP | 0 916 361 A1 | 5/1999 |
| EP | 0 931 560 A1 | 7/1999 |
| EP | 0937475 A2 | 8/1999 |

| | | | | | | |
|---|---|---|---|---|---|---|
| EP | 0 956 879 | A1 | 11/1999 | WO | WO 01/93926 A2 | 12/2001 |
| EP | 1 045 145 | A1 | 10/2000 | WO | WO 01/93926 A2 | 12/2001 |
| EP | 1 060 757 | A1 | 12/2000 | WO | WO 02/02165 A2 | 1/2002 |
| EP | 1 086 718 | A1 | 3/2001 | WO | WO 02/07804 A1 | 1/2002 |
| EP | 1 125 593 | A1 | 8/2001 | WO | WO 02/40083 A2 | 5/2002 |
| EP | 1 167 765 | A2 | 1/2002 | WO | WO 02/46080 A1 | 6/2002 |
| EP | 0 775 501 | B1 | 6/2002 | WO | WO 02/053220 A2 | 7/2002 |
| EP | 0 894 216 | B1 | 7/2003 | WO | WO 02/066854 A1 | 8/2002 |
| EP | 1329233 | B1 | 7/2003 | WO | WO 02/068014 A3 | 10/2002 |
| EP | 1350537 | A1 | 10/2003 | WO | WO 02/081012 A2 | 10/2002 |
| EP | 1 360 970 | A1 | 11/2003 | WO | WO 02/081013 A2 | 10/2002 |
| EP | 1 380 315 | A1 | 1/2004 | WO | WO 02/083206 A2 | 10/2002 |
| EP | 1407747 | A1 | 4/2004 | WO | WO 02/094352 A2 | 11/2002 |
| EP | 1407793 | A1 | 4/2004 | WO | WO 02/100457 A2 | 12/2002 |
| EP | 1421968 | A2 | 5/2004 | WO | WO 02/102442 A1 | 12/2002 |
| EP | 1177802 | B1 | 9/2004 | WO | WO 03/015860 A1 | 2/2003 |
| EP | 1 475 113 | A | 11/2004 | WO | WO 03/026728 A | 4/2003 |
| EP | 1495775 | A1 | 1/2005 | WO | WO 03/068305 A1 | 8/2003 |
| EP | 1502613 | A1 | 2/2005 | WO | WO 03/075980 A2 | 9/2003 |
| EP | 1525873 | A1 | 4/2005 | WO | WO 03/095003 A1 | 11/2003 |
| EP | 1527792 | A1 | 5/2005 | WO | WO 2004/012796 A1 | 2/2004 |
| EP | 1616594 | A1 | 1/2006 | WO | WO 2004/029457 A1 | 4/2004 |
| EP | 1704889 | A1 | 9/2006 | WO | WO 2004/030726 A1 | 4/2004 |
| EP | 1762259 | A1 | 5/2007 | WO | WO 2004/037325 A1 | 5/2004 |
| FR | 576849 | | 8/1924 | WO | WO 2004/054644 A1 | 7/2004 |
| FR | 2 611 013 | A1 | 8/1988 | WO | WO 2004/064593 A2 | 8/2004 |
| FR | 2725902 | A1 | 10/1994 | WO | WO 2004/071308 A1 | 8/2004 |
| FR | 2733915 | A1 | 11/1996 | WO | WO 2004/087240 A1 | 10/2004 |
| FR | 2 752 164 | A | 2/1998 | WO | WO 2004/098683 A1 | 11/2004 |
| FR | 2 752 164 | A1 | 2/1998 | WO | WO 2004/101016 A1 | 11/2004 |
| FR | 2781617 | A1 | 1/2000 | WO | WO 2004/101071 A2 | 11/2004 |
| GB | 478803 | | 1/1938 | WO | WO 2005/002649 A1 | 1/2005 |
| GB | 591730 | | 3/1946 | WO | WO 2005/004973 A1 | 1/2005 |
| GB | 906574 | | 9/1962 | WO | WO 2005/018703 A1 | 3/2005 |
| GB | 1 268 575 | | 3/1972 | WO | WO 2005/037184 A2 | 4/2005 |
| GB | 1 403 034 | | 8/1975 | WO | WO 2005/037350 A2 | 4/2005 |
| GB | 2 088 215 | A | 6/1982 | WO | WO 2005/039673 A2 | 5/2005 |
| GB | 2 224 808 | A | 5/1990 | WO | WO 2005/046780 A1 | 5/2005 |
| GB | 2 230 702 | A | 10/1990 | WO | WO 2005/065748 A1 | 7/2005 |
| GB | 2 270 552 | A | 3/1994 | WO | WO 2005/068006 A1 | 7/2005 |
| JP | A-03-191965 | A | 8/1991 | WO | WO 2005/092410 A1 | 10/2005 |
| JP | 5326062 | A | 12/1993 | WO | WO 2005/094920 A1 | 10/2005 |
| JP | 7051251 | | 11/1995 | WO | WO 2005/118055 A1 | 12/2005 |
| JP | A-08-187286 | A | 7/1996 | WO | WO 2006/003130 A1 | 1/2006 |
| JP | A-10-179734 | A | 7/1998 | WO | WO 2006/015507 A2 | 2/2006 |
| JP | 2000059877 | A | 2/2000 | WO | WO 2006/015600 A2 | 2/2006 |
| JP | 3140740 | B2 | 3/2001 | WO | WO 2006/024650 A2 | 3/2006 |
| JP | 2002-028246 | | 1/2002 | WO | WO 2006/032689 A1 | 3/2006 |
| NL | 1017427 | C | 11/2002 | WO | WO 2006/032692 A1 | 3/2006 |
| WO | WO 81/01795 | A1 | 7/1981 | WO | WO 2006/061027 A2 | 6/2006 |
| WO | WO 82/03558 | A1 | 10/1982 | WO | WO 2006/061354 A1 | 6/2006 |
| WO | WO 87/06474 | A1 | 11/1987 | WO | WO 2006/075016 A1 | 7/2006 |
| WO | WO 9204062 | A1 | 3/1992 | WO | WO 2006/077262 A1 | 7/2006 |
| WO | WO 93/03787 | A1 | 3/1993 | WO | WO 2006/077263 A1 | 7/2006 |
| WO | WO 93/05840 | A2 | 4/1993 | WO | WO 2006/089958 A1 | 8/2006 |
| WO | WO 93/11709 | A1 | 6/1993 | WO | WO 2006/097111 A2 | 9/2006 |
| WO | WO 94/20160 | A1 | 9/1994 | WO | WO 2006/108775 A1 | 10/2006 |
| WO | WO 95/28327 | A1 | 10/1995 | WO | WO 2006/121921 A2 | 11/2006 |
| WO | WO 96/20021 | A1 | 7/1996 | WO | WO 2006/122048 A1 | 11/2006 |
| WO | WO 96/32981 | A1 | 7/1996 | WO | WO 2007/000162 A2 | 1/2007 |
| WO | WO 96/35472 | A1 | 11/1996 | WO | WO 2007/002523 A2 | 1/2007 |
| WO | WO 98/09065 | A1 | 3/1998 | WO | WO 2007/020090 A1 | 2/2007 |
| WO | WO 98/26835 | A1 | 6/1998 | WO | WO 2007/065944 A1 | 6/2007 |
| WO | WO 98/33549 | A1 | 8/1998 | WO | WO 2007/071255 A1 | 6/2007 |
| WO | WO 98/58693 | A1 | 12/1998 | WO | WO 2007/071258 A1 | 6/2007 |
| WO | WO 99/07435 | A1 | 2/1999 | WO | WO 2007/093051 A1 | 8/2007 |
| WO | WO 99/33504 | A1 | 7/1999 | WO | WO 2007/093182 A2 | 8/2007 |
| WO | WO 99/36009 | A1 | 7/1999 | WO | WO 2007/140631 A1 | 12/2007 |
| WO | WO 99/56802 | A1 | 11/1999 | WO | WO 2007/140783 A2 | 12/2007 |
| WO | WO 99/61815 | A1 | 12/1999 | WO | WO 2007/140785 A1 | 12/2007 |
| WO | WO 00/02614 | A1 | 1/2000 | WO | WO 2007/141210 A1 | 12/2007 |
| WO | WO 00/03757 | A1 | 1/2000 | WO | WO 2008/014791 A1 | 2/2008 |
| WO | WO 00/44324 | A1 | 8/2000 | WO | WO 2008/014792 A1 | 2/2008 |
| WO | WO 01/04507 | A1 | 1/2001 | WO | WO 2008/048631 A1 | 4/2008 |
| WO | WO 01/30419 | A2 | 5/2001 | WO | WO 2008/052545 A1 | 5/2008 |
| WO | WO 01/68180 | A1 | 9/2001 | WO | WO 2008/092782 A1 | 8/2008 |
| WO | WO 01/72353 | A2 | 10/2001 | WO | WO 2008/092958 A2 | 8/2008 |
| WO | WO 01/076684 | A1 | 10/2001 | WO | WO 2008/092959 A1 | 8/2008 |
| WO | WO 01/81785 | A1 | 11/2001 | WO | WO 2008/135098 A1 | 11/2008 |

| | | |
|---|---|---|
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |

OTHER PUBLICATIONS

International Preliminary Report on Patentability dated Mar. 14, 2006 for International Application No. PCT/DK2005/000190.
"Why inset®?" inset® infusion set product overview; http://web.archive.org/web/20040906102448/http://www.infusion-set.com/Default.asp?ID=108; two pages.

* cited by examiner

FIG. 15
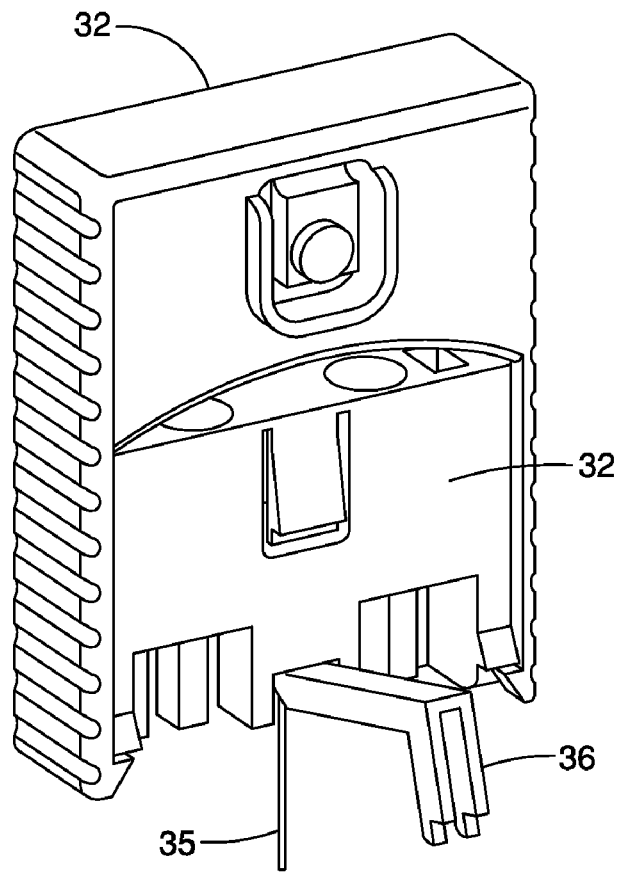
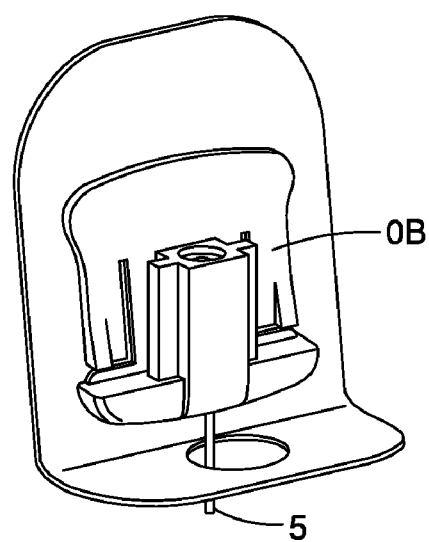

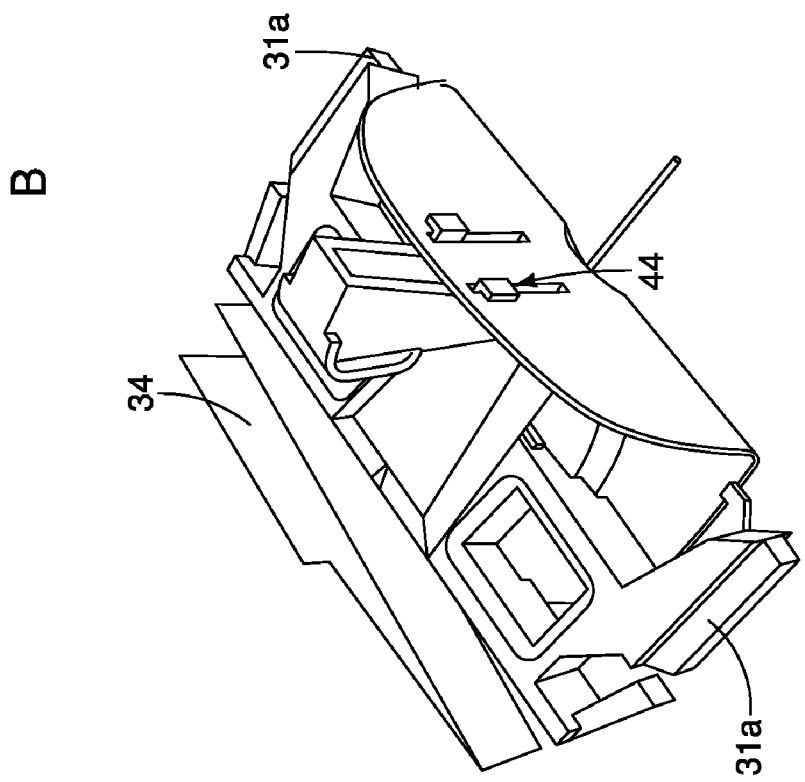
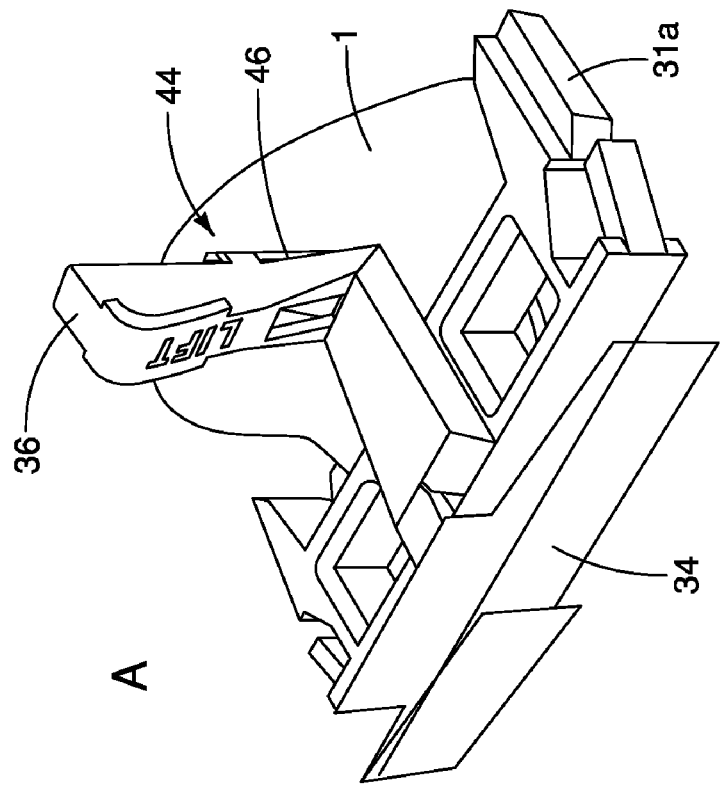
FIG. 23

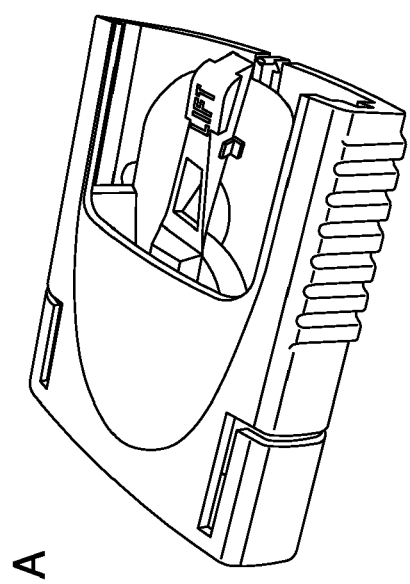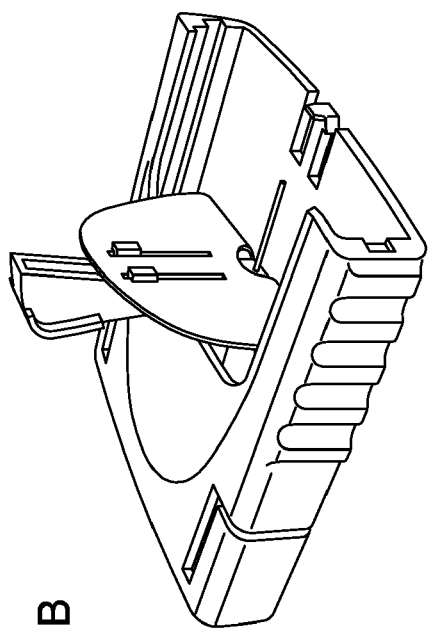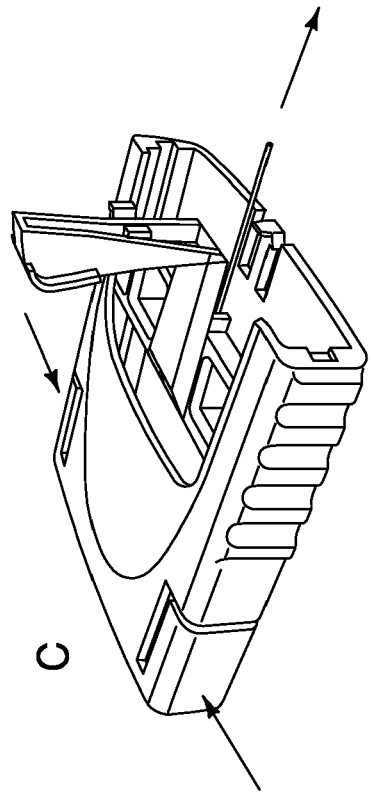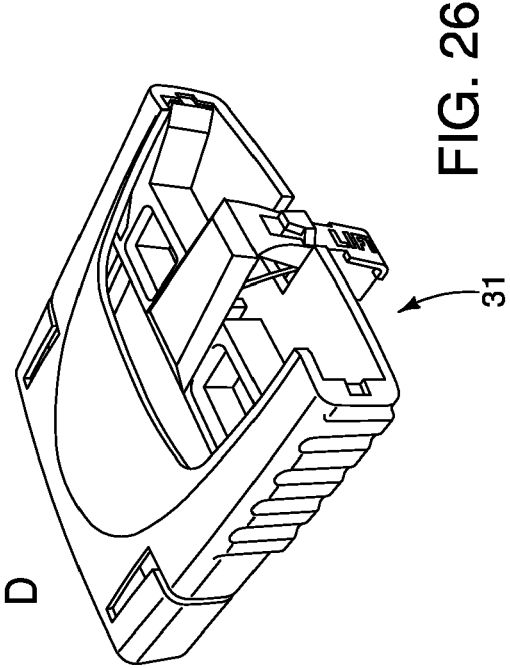
FIG. 26

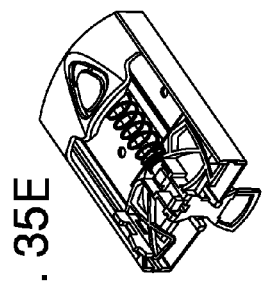
FIG. 35A
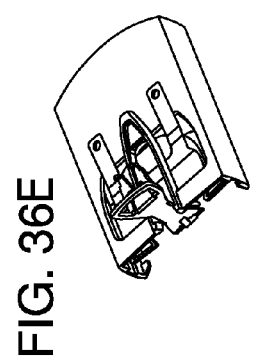
FIG. 36A
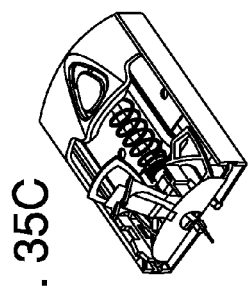
FIG. 35B
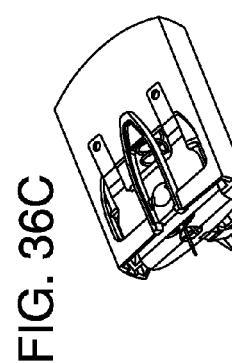
FIG. 36B
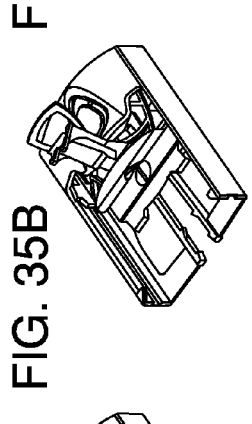
FIG. 35C
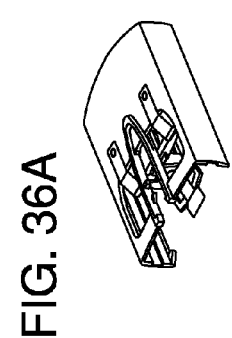
FIG. 36C
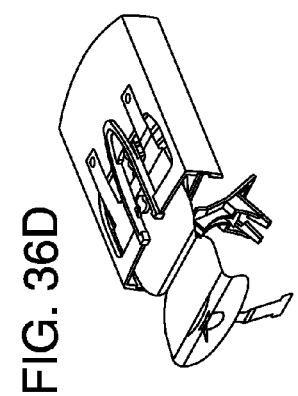
FIG. 35D
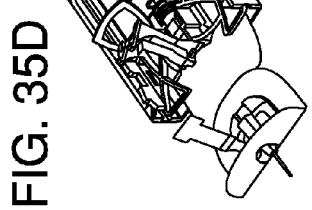
FIG. 36D
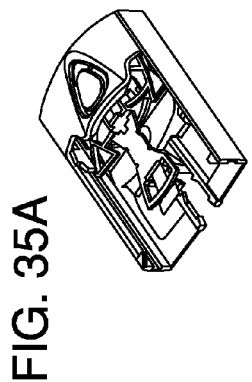
FIG. 35E
FIG. 36E

INJECTION DEVICE FOR INFUSION SET

This application is a national phase application based on PCT/DK2005/000190, filed Mar. 21, 2005, which claims the benefit of U.S. Provisional Application No. 60/556,863, filed Mar. 26, 2004 and Danish Patent Application No. PA 200400493, filed Mar. 26, 2004, these references are incorporated herein in their entirety.

THE TECHNICAL FIELD

The invention relates to an injector device for an infusion set for intermittent or continuous administration of a therapeutical substance, such as insulin. An infusion set comprises an infusion part with a cannula to penetrate the skin of a person and a connector for connecting the infusion part with a medical device preferably a medical delivery device such as an insulin pump.

The infusion set has in its assembled form a substantially planar rear side and a relatively large width compared to its thickness, thus allowing it to lie flat on the patient's skin and thereby minimizing the discomfort of carrying the infusion set.

The injector device according to the present invention is especially directed towards situations where patients wants to or has to insert the infusion part by themselves without the assistance of educated personnel.

PRIOR ART

U.S. Pat. No. 5,522,803 discloses an infusion set having an infusion part and a connector. The infusion part comprises a soft plastic cannula in liquid communication with a cavity for receiving a needle from a connector, two sloping guiding holes and two retention devices; and the connector comprises a cannula, two square guiding pins and two arms with a hooking part for gripping the retention device of the infusion part and operating in the main plane of the infusion part.

A lot of patients e.g. insulin patients have to or may desire to insert an infusion device or to place a subcutaneous sensor or the like themselves. For some persons it is a troublesome process to perform the skin penetration themselves, they therefore need a device which assists them in this process and thereby making the process less problematic.

The document US 2003/0225373 discloses an insertion device for inserting an infusion part or a sensor into a patient. The device comprises a housing, a coil spring, a safety device and part for angling the insertion into the patient. However the apparatus is relatively complicated to manufacture industrially and further the device has to be loaded manually by the patient by a rather complicated procedure.

WO 03/026728 A1 discloses an injector device comprising a housing, a spring, a slidable bar, a locking mechanism and a needle.

It is an object of the invention to provide an improved insertion device which is easy to manufacture and which is suitable for being delivered in a loaded form or at least being easier to load. Especially elderly people, who can have some motor problems, need an insertion device which exists in a pre-loaded form.

According to the invention an injector device is provided for the subcutaneous introduction of a cannula of an infusion part into the skin of a patient. The injector device comprises a housing, a back and longitudinally extending guiding means, a member which is longitudinally slidable within the housing, an insertion needle for insertion in the cavity of said cannula, a spring located between the back of the housing and the longitudinally slidable member, locking means for maintaining the spring in a compressed state and release means for disengaging the locking means characterized in that the device further comprises a pivoting member which can be swung from a position in which the pivoting member allows for insertion of the needle into a position in which the pivoting member embraces the needle.

The insertion device according to this invention is easy to handle in a safe way before, during and after use, even if the user has reduced dexterity in the hands. Also the user can choose an essentially vertical insertion which makes it easier to control the dept of the needle penetration and thereby the insertion dept of the cannula. This is important in self-insertion of the infusion part. Besides the injector is of a very simple construction which makes it possible to reduce costs of production.

The insertion needle can during insertion be unreleasably attached to the slidable member, unreleasably attached to the infusion part thereby being the cannula or the insertion needle can be a separate unit which the user removes after insertion.

In a preferred embodiment the pivoting member is fastened to the slidable member. This makes production of the unit simpler, and also the pivoting member will need to be shorter than if the pivoting member was fastened to the housing. If the pivoting member is fastened to the slidable member, the position where the pivoting member allows for insertion of the needle is preferably in an angle v where v≈45° or larger in order for the pivoting member to be bend backwards when touching the user, preferably v≈90° or larger in order for the pivoting member not to hit the user during insertion. The angle v is the angle between the central axis of the injection device which is parallel to the insertion needle, and the pivoting member.

In a preferred embodiment the insertion device has means for temporarily fixing the pivoting member in an essentially right angle relative to the housing thus stabilizing the insertion device in an essentially vertical position relative to the skin to be penetrated prior to penetration. This is particularly relevant for patients with motor problems since they can have problems to control the insertion angle.

Preferably the housing has means for getting a better grip of the injector device. Examples of such means could be but are not limited to rims, grooves, recesses, a roughened surface optionally of another material than the housing itself, preferably recesses are used There will be different possibilities for placing the pivoting member in the position where it embraces the needle but in a preferred embodiment the pivoting member embraces the needle when the slidable member is in a forward position and the spring is in a released state. Often when using injection devices in connection with insertion of infusion sets the user is supposed to bring the insertion needle back into the housing in order to protect the surroundings from the used insertion needle. This means the users has to work against the spring force, which was pushing the needle forward during insertion, and at the same time the user has to avoid the used needle, when bringing it back into the housing. This can be quite difficult for a user which might have reduced dexterity of the hands and fingers. According to the present invention it will be quite easy for the user to secure the insertion needle as turning the relatively large pivoting member does not call for the use of strength.

In one embodiment the insertion needle is destroyed and secured as the pivoting member is placed in a final position embracing the needle. This will make it safe to dispose of the used insertion device with ordinary garbage.

In one embodiment the pivoting arms are also the locking means and it has a tab functioning as disengaging means.

In another embodiment there is separate locking means and disengaging means. Preferably the pivoting member then still have a tab for securing the arm in a position parallel to the axis of the housing until it is desired to swing the pivoting member to the position in which it embraces the needle.

Preferably the pivoting member embraces the needle in a first position being parallel to the main axis of the injector device then it is swung into a second position being essentially orthogonal to said main axis and then finally swung into a position in which it embraces the needle.

In a preferred embodiment the pivoting member is swung from the position essentially orthogonal to said main axis, 180 degrees to another position embracing the needle and being secured in this position said position also being essentially orthogonal to the main axis. Optionally the needle is destroyed in the process and secured in the pivoting member.

In another preferred embodiment the infusion part to be inserted is provided with an adhesive support unreleasably fastened to the infusion part and having an adhesive surface, which adhesive surface is provided with a release liner.

In this embodiment the pivoting member can have fixing means for releasably fastening a part of the adhesive support to the pivoting member. This construction assures that the adhesive support is folded in an appropriate way during insertion, which results in that the adhesive support will turn a part of the adhesive surface towards the user's skin, when the infusion part is inserted.

In another preferred embodiment the release liner of the adhesive support can also have one or more projecting parts. Describing parts as projecting from the release liner means that the parts are not necessarily in contact with the adhesive surface of the adhesive support, the projecting part or parts extend beyond the part of the release liner being in protecting contact with the adhesive surface. One of the projecting parts can be fastened unreleasably to the housing in order to at least partly have the release liner removed from the adhesive support during insertion of the needle. The total removal of the release liner will take place after insertion of the needle when the injector device is taken away for disposal and the release liner will—as it is still attached to the injection device—be removed and disposed off together with the used injector device.

In a more preferred embodiment the release liner comprises at least two separate pieces, and each piece has at least one projecting part. This makes it possible to remove the release liner automatically during insertion without the release liner coming into conflict with the insertion needle.

Preferably the projecting part of the first piece of release liner is attached to the pivoting member during insertion and the projecting part of the second piece of release liner is attached to the housing during insertion. This embodiment makes it easier for the user to remove the release liner during/after insertion and at the same time the adhesive surface of the adhesive support is completely protected before insertion.

In a preferred embodiment of the invention the pivoting member of the injector device further has means for temporarily fixing the adhesive support of the infusion part. Hereby it is achieved that the adhesive support does not fold in an unsuitable manner during insertion of the infusion part.

Preferably the injector device comprises means for stopping the slidable member in its most forward position preferably in form of a stopping tab.

In a preferred embodiment the injector device has a locking tab for fixing the pivoting member in a position embracing the needle.

In the following the invention will be described in further details with reference to the figures.

FIG. 15 shows the second embodiment of the injector device after separating the injector from the infusion part.

Figure 21:
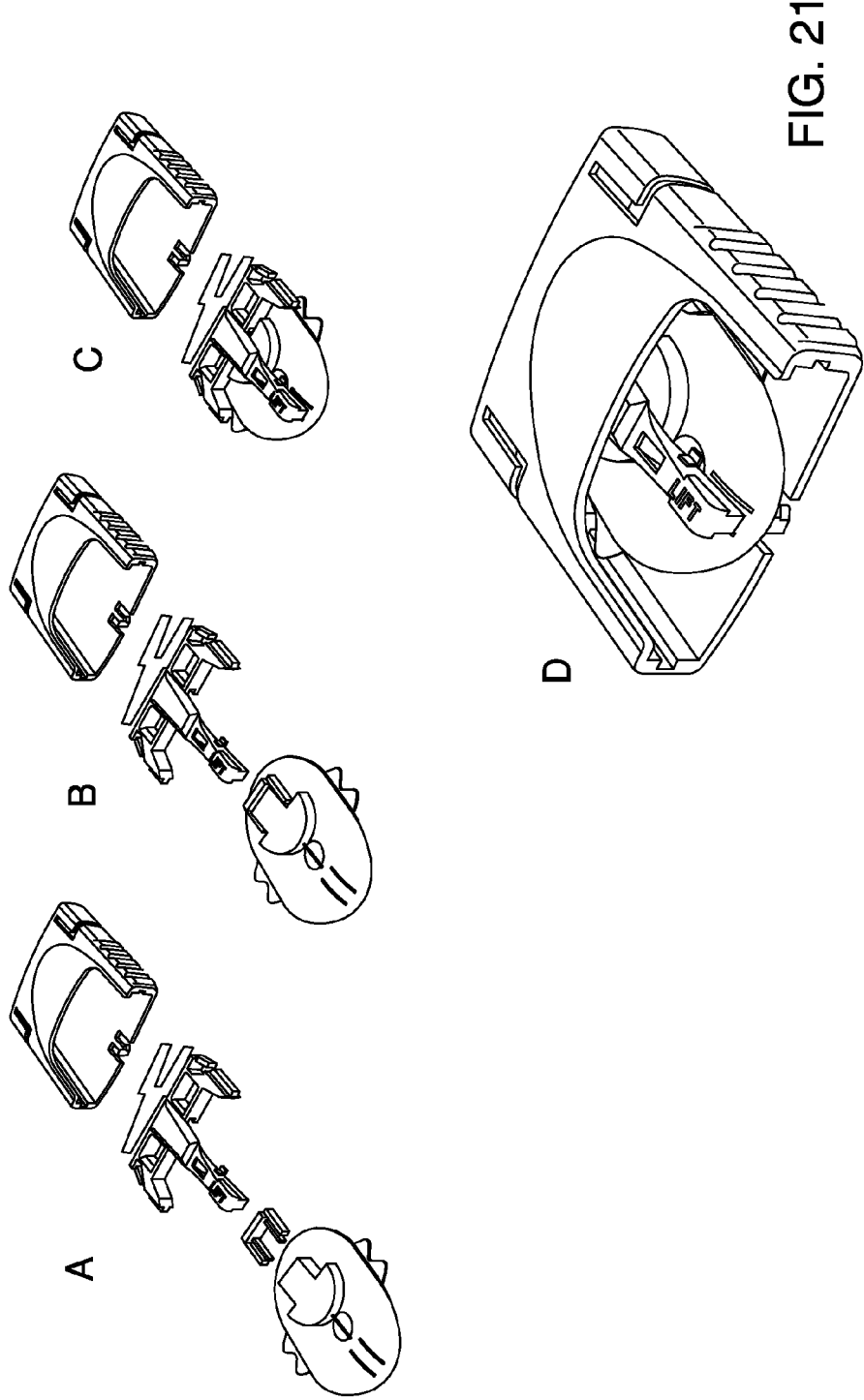

FIG. 21 A-D shows assembling of the infusion part and injector device according to the third embodiment.

Figure 22:
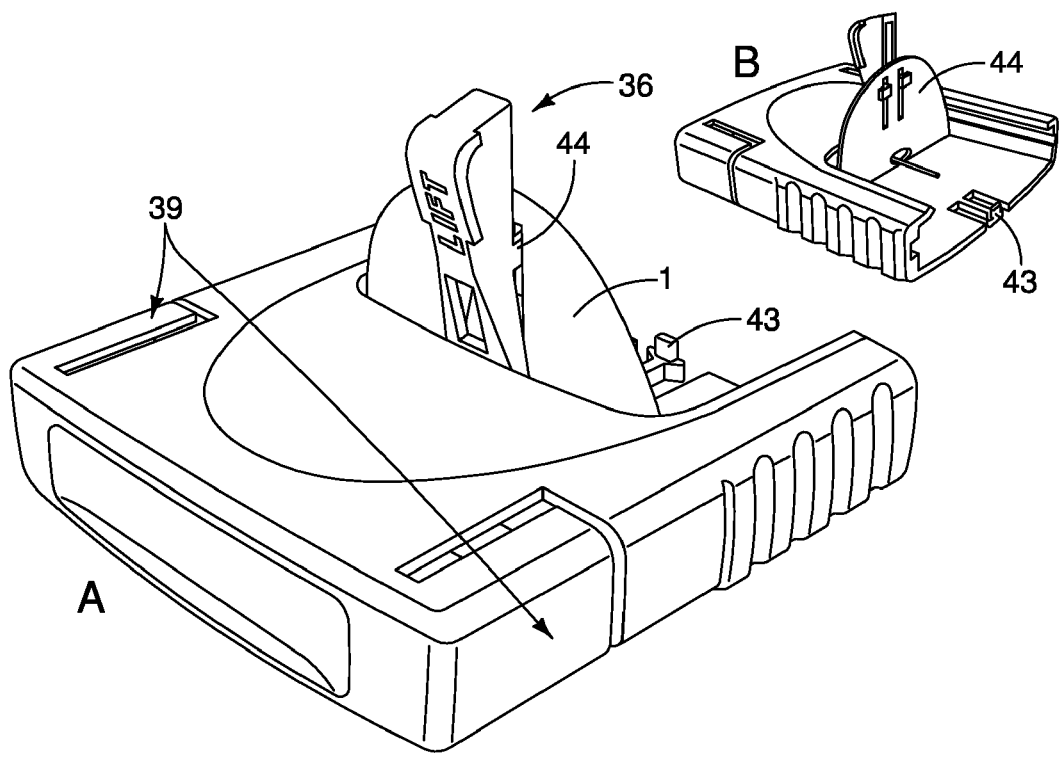

FIG. 22 A-B shows the third embodiment of the injector device prepared for insertion.

FIG. 23 A-B shows the adhesive support of the infusion part hooked to the slidable member.

Figure 24:
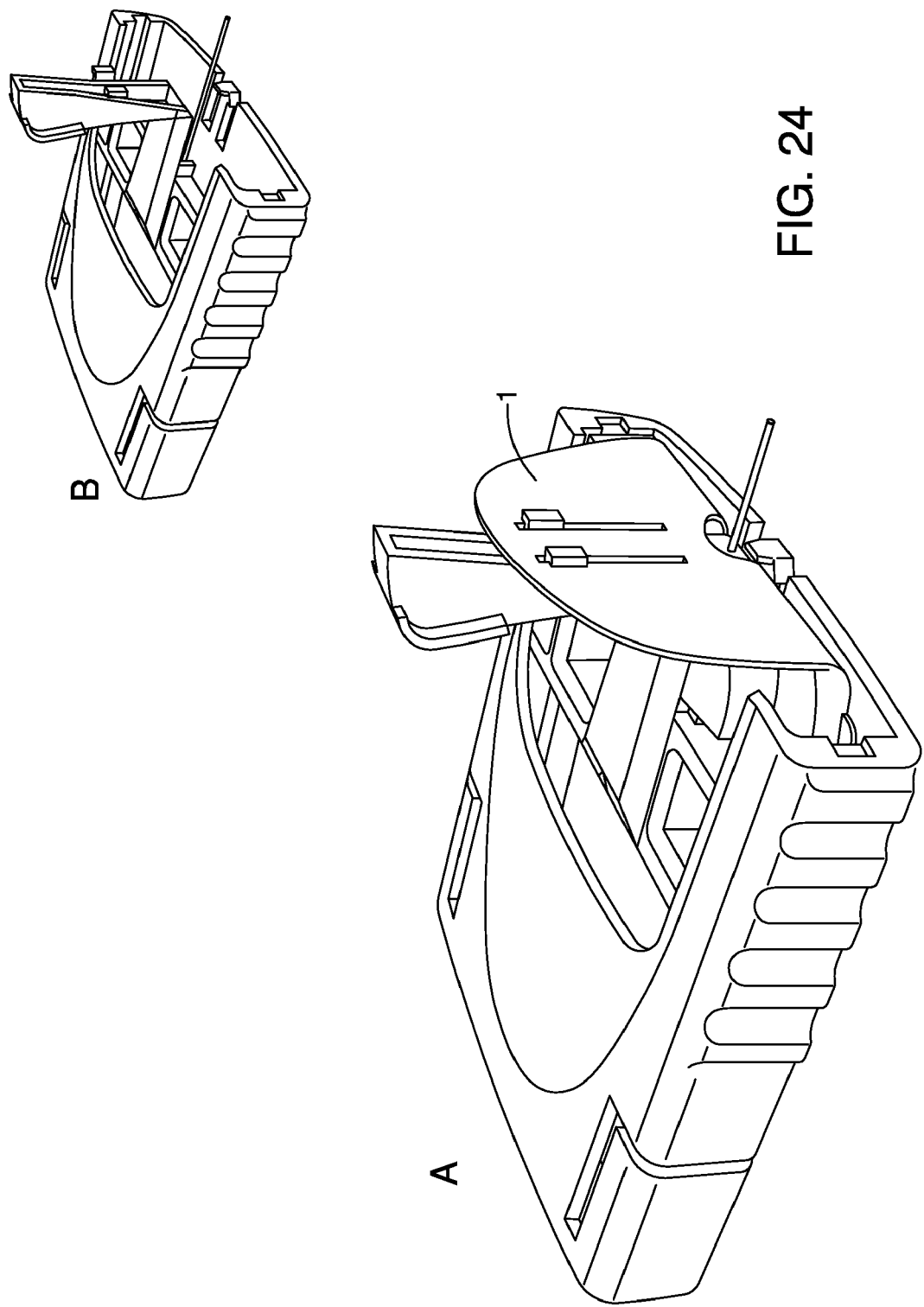

FIG. 24 A shows the injector device after insertion with an infusion part and

FIG. 24 B shows the injector device after insertion without the infusion part.

Figure 25:
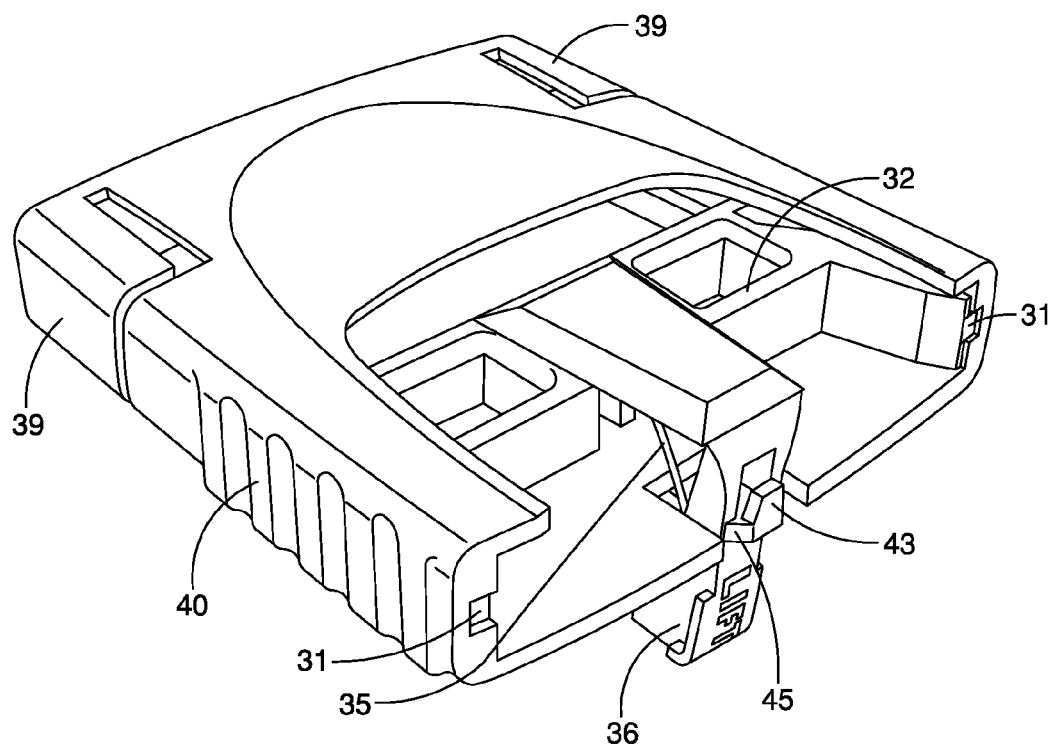

FIG. 25 shows the third embodiment of the injector device after insertion and embracing the needle.

FIG. 26 A-D shows the different steps when injecting the infusion part.

FIGS. 35 and 36 A-E shows the different steps when using a fifth embodiment of the injector device for injecting the infusion part.

Figure 1:
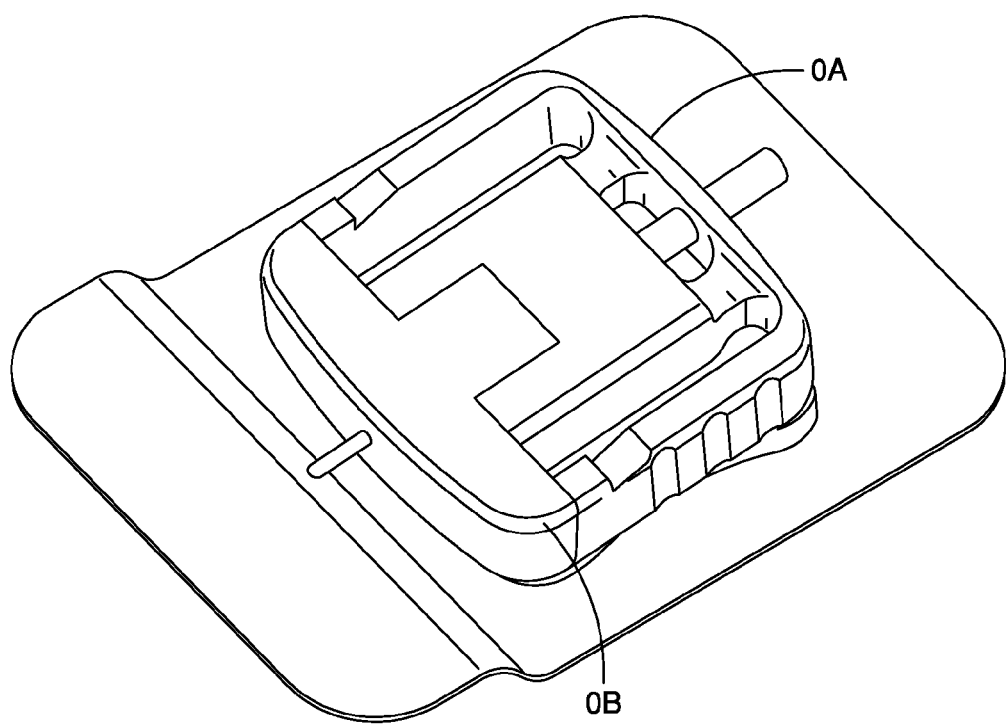
FIG. 1 shows one embodiment of an infusion set where the infusion part and the connector are unified.
Figure 2:
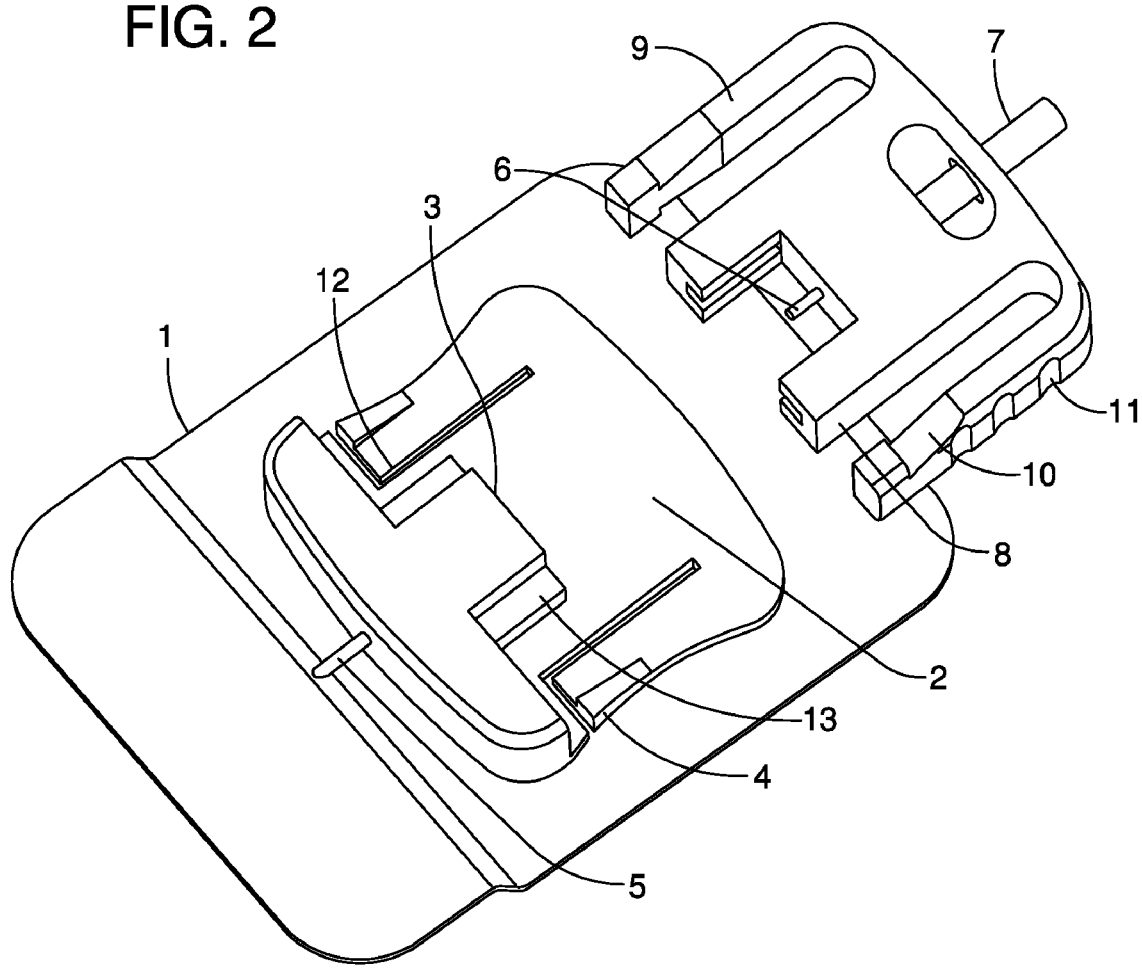
FIG. 2 shows one embodiment of the infusion set where the infusion part and the connector are separated.
Figure 3:
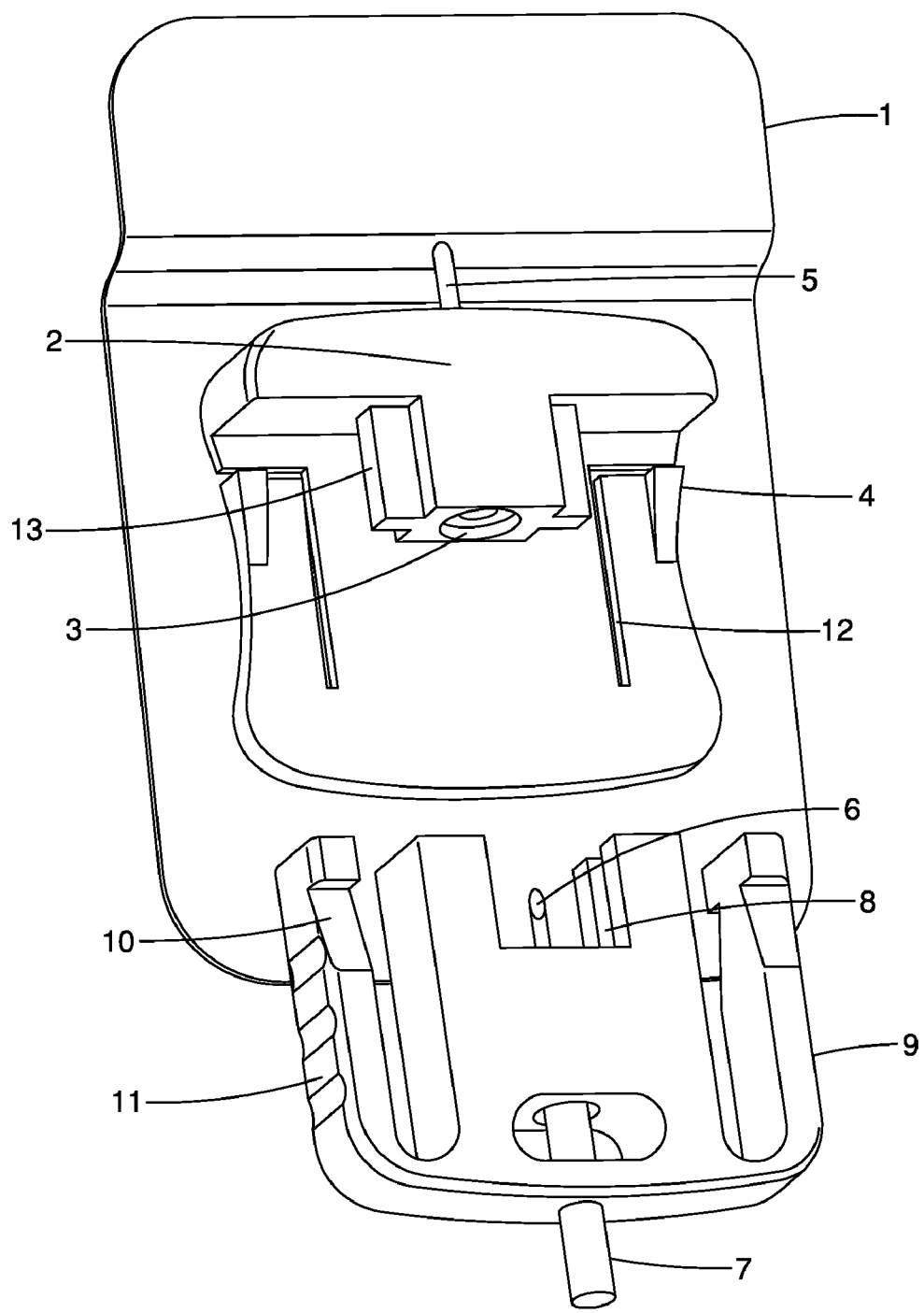
FIG. 3 shows the same embodiment of the separated infusion set as in FIG. 2 from a different angle.
Figure 4:
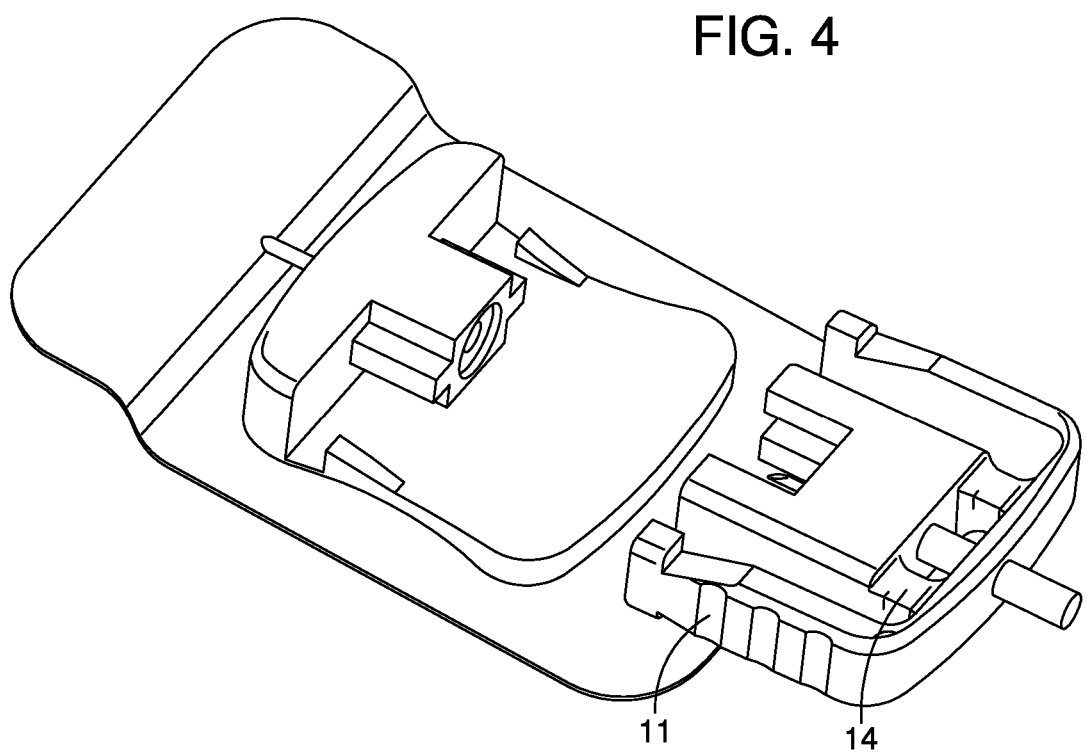
FIG. 4 shows a second embodiment of a separated infusion set from a first angle.
Figure 5:
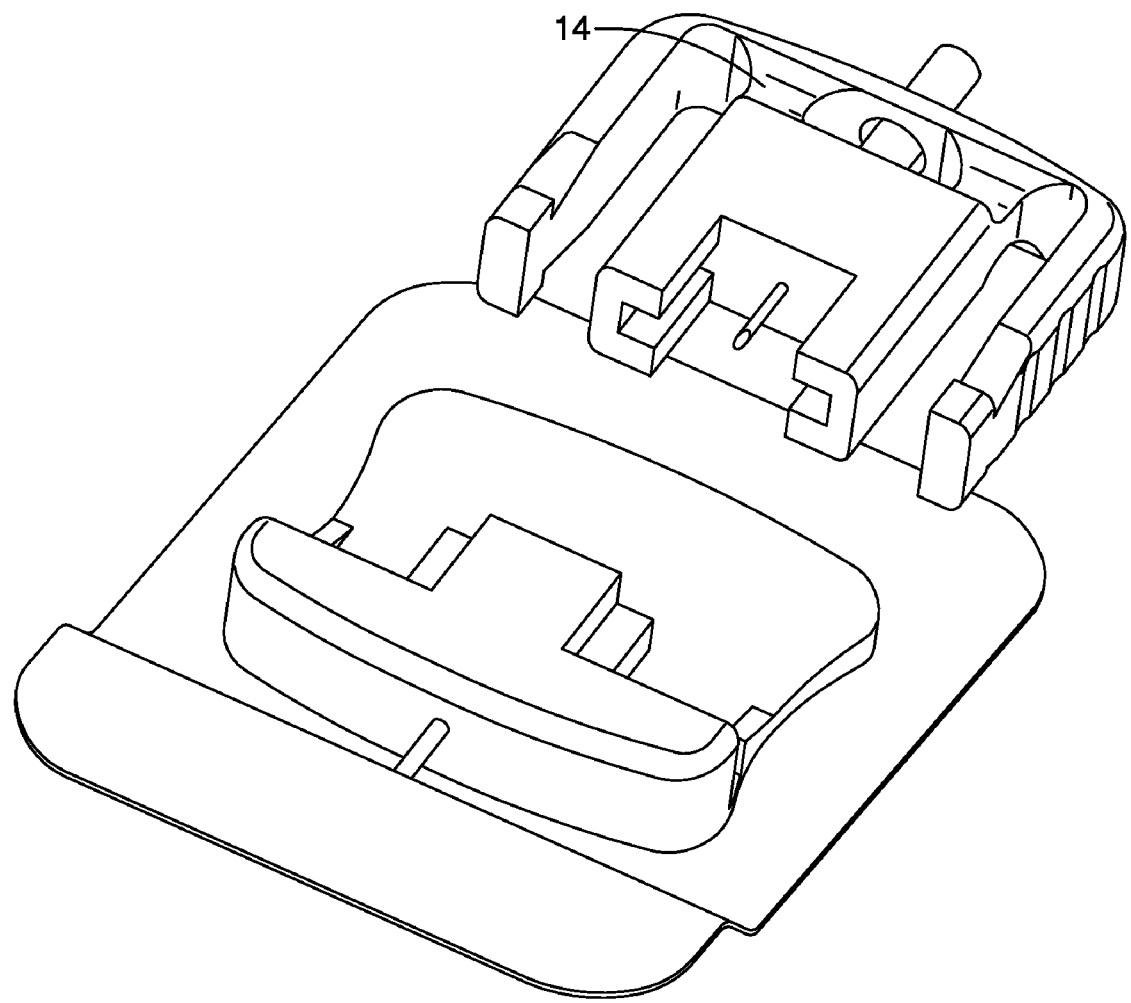
FIG. 5 shows the second embodiment of the infusion set from a different angle.

FIG. 1-3 illustrates an embodiment of an infusion set. The infusion set comprises an infusion part (0B) and a connector (0A). The infusion part (0B) comprises a base part (2) having a main plane which, when the infusion set is attached to a patient, is essentially parallel with the skin of the patient. Said base part (2) comprises a first set of guiding means (13) which in this case has the form of two stabilizing fins. The base part further comprises two retention devices (4) extending from the upper surface of the base part in this case in form of two steps. Mounted on the inner surface of the infusion part is an adhesive support (1) which in this case is a plaster. A cannula (5) is extending from the base part (2) and is penetrating the adhesive support (1) being in fluid communication with a central cavity (3). The cannula (5) is preferably a soft cannula but could also be made of metal. The cavity (3) optionally being covered by a membrane is adapted to receive a cannula (6) extending from the connector. In the embodiment shown in FIG. 2-5 the cannula (6) is extending from the central part of the connector and is placed in a retracted position relative to the front of the central part. In this embodiment the base part (2) has two cuttings (12) creating two flaps on which the retention devices (4) are mounted. The connector (0A) comprises two arms (9) having four carvings (10) adapted to fit with the retention devices (4). The connector (0A) is symmetrical around the main plane and around the plane perpendicular to the main plane and parallel to the main axis thus allowing the connector to match with the base part in two ways. The cannula (6) is in fluid communication with the tube (7) which provides the connection to a medical device such as an insulin pump. In this embodiment the central part of the connector has a second set of guiding means (8) in form of two grooves placed symmetrically around the main plane of the connector. In this embodiment the connector further has gripping means (11) in form of recesses. The gripping means 11 are optional and can be selected from the group consisting of rims, grooves, recesses or a roughened surface optionally of another material than the connector itself FIGS. 4 and 5 show another embodiment of the invention where the connector has two grooves (14) which in this case are placed symmetrically around the main plane of the connector. However it is not necessary for the grooves to be places symmetrically around the main plane since they are not coupling with the infusion part.

Whether the infusion set is intended to be inserted manually or by an injector the infusion part (0B) and the connector (0A) are delivered to the user as two separate units in sterile packages. If inserted manually the infusion part (0B) will at delivery be combined with a needle unit with the same locking and guiding means (8) as the connector. The needle unit is provided with an insertion needle extending from the central front which insertion needle at delivery extends through and beyond the end of the cannula (5). The needle unit's only function will be to penetrate the user's skin where after the needle unit is removed and replaced with the connector (0A) leaving the cannula (5) subcutaneous.

The connector (0A) can be connected to a luer coupling member through the tube (7). Through the luer coupling it is possible to administer a suitable therapeutical substance, such as insulin from a pump. The connector can also be a sort of closing part with a suitable entrance for the inserting needle of a syringe. Such a closing part can stay in position for up till three days while the user can have medication, e.g. insulin injected through the entrance in order to reduce trauma to the skin.

It is important for the user that it is easy to change i.e. to engage and to disengage the infusion part (0B) and the connector (0A) even when the user has reduced dexterity of hands and fingers. The present infusion set complies with this purpose as the movement used to unlock the infusion part (0B) from the connector (0A) is pressing the connector between the first finger and the thumb which is a simple and easily performed movement. Also the oppositely directed forces from respectively the first finger and the thumb pushing toward each other, are not only used to unlock the device but is also used when pulling the connector away from the infusion part (0B). In order to make it easier to disengage the connector (0A) the arms (9) can be made very flexible, either by choosing a soft and flexible material or by making the fastening of the arms (9) to the central part more or less rigid e.g. by varying the size of the grooves (14) on the shoulder of the connector (0A).

Although the arms (9) are very flexible the danger of accidently releasing and pulling the connector away from the infusion part, when positioned on the skin of the user, is quite small as the device has to be exposed to a simultaneous pressure from both sides.

Figure 6:
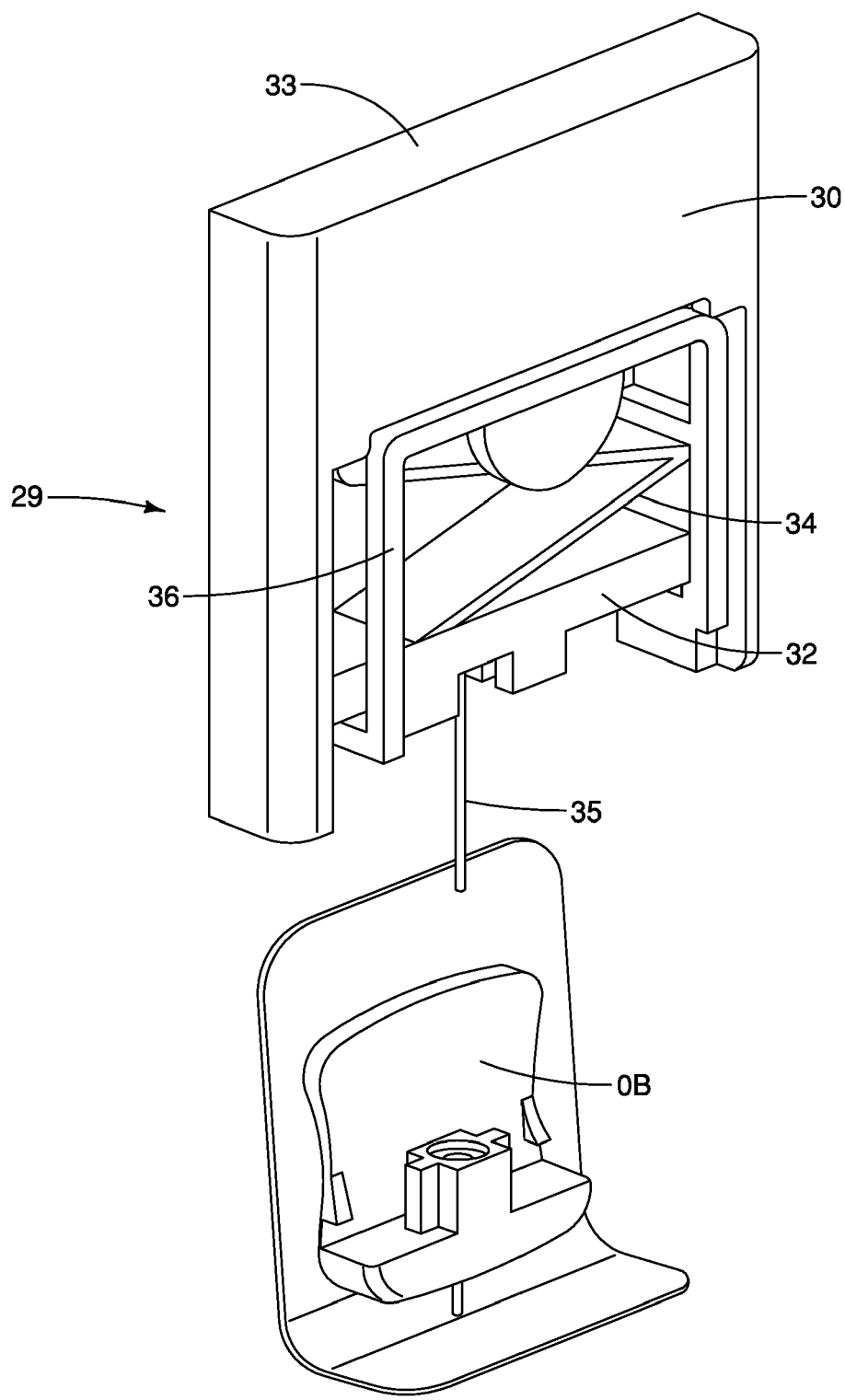
FIG. 6 shows a first embodiment of an injector device separated from the infusion part.
Figure 7:
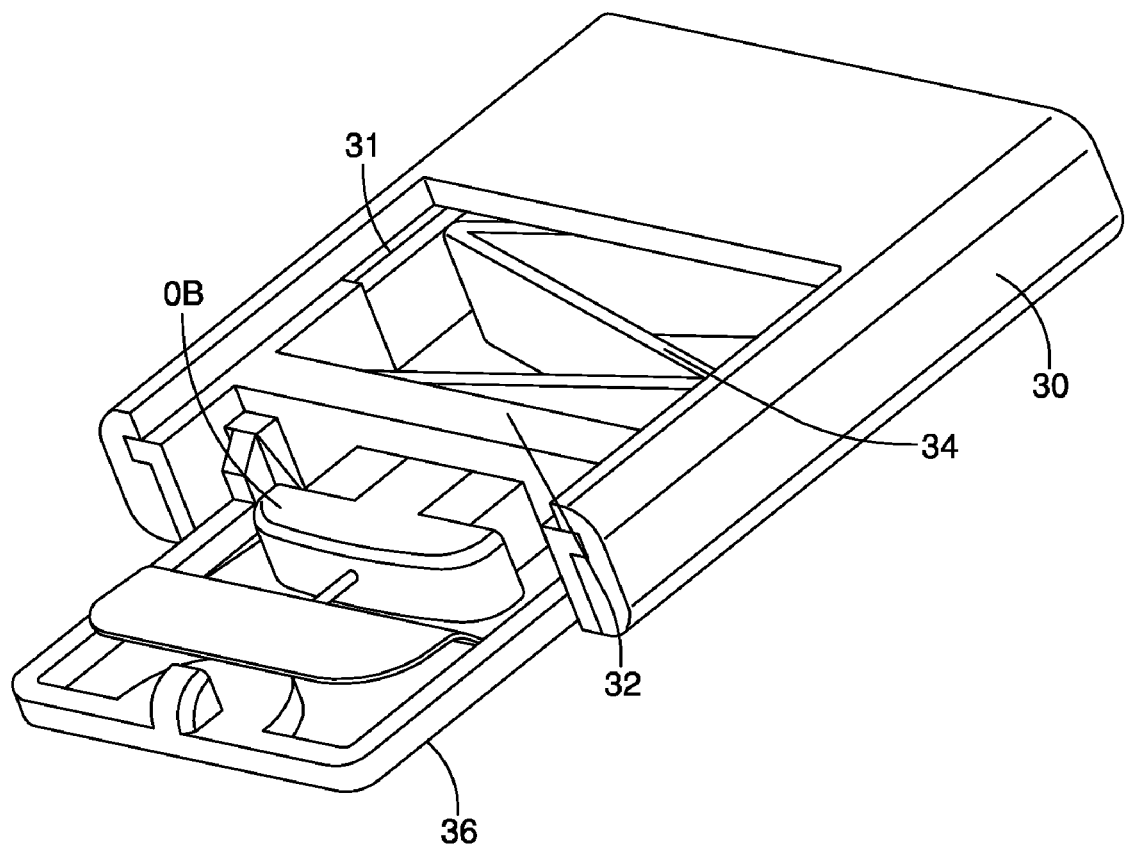
FIG. 7 shows the first embodiment of the injector device joined with the infusion part.
Figure 8:
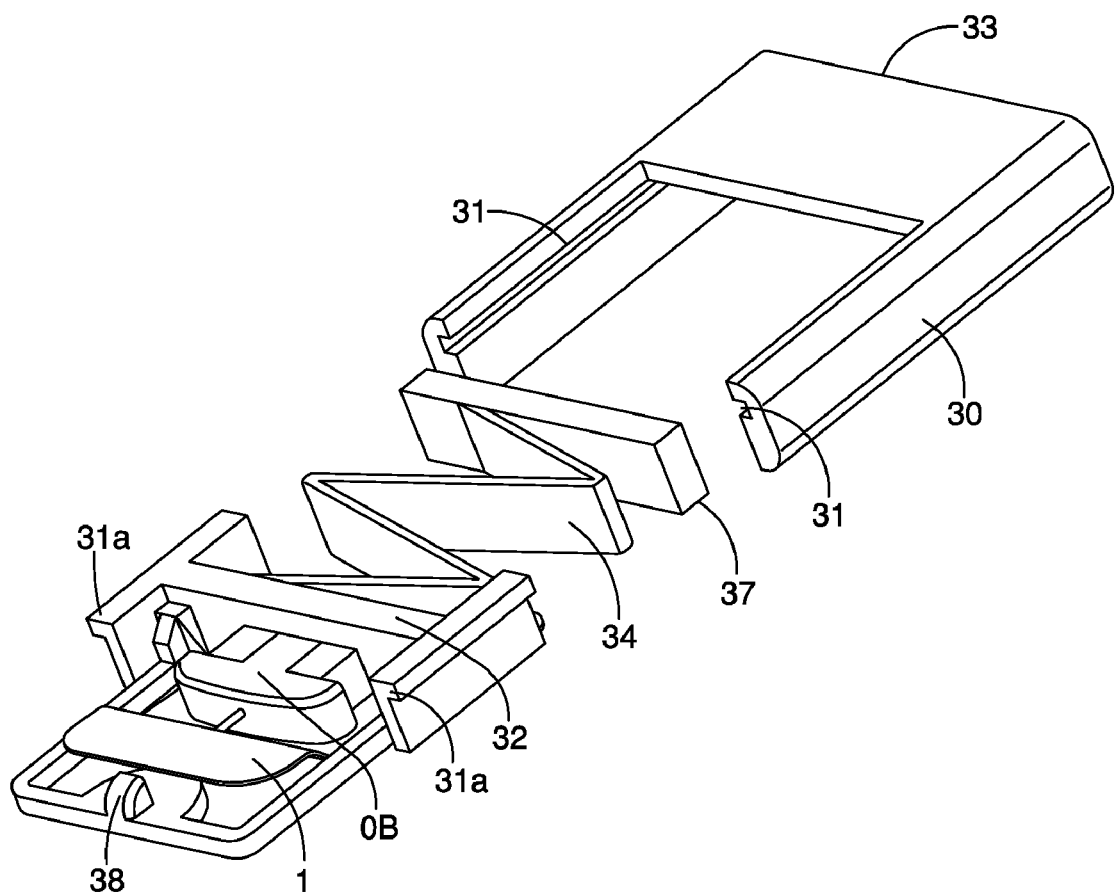
FIG. 8 shows the first embodiment of the injector device joined with the infusion part.
Figure 9:
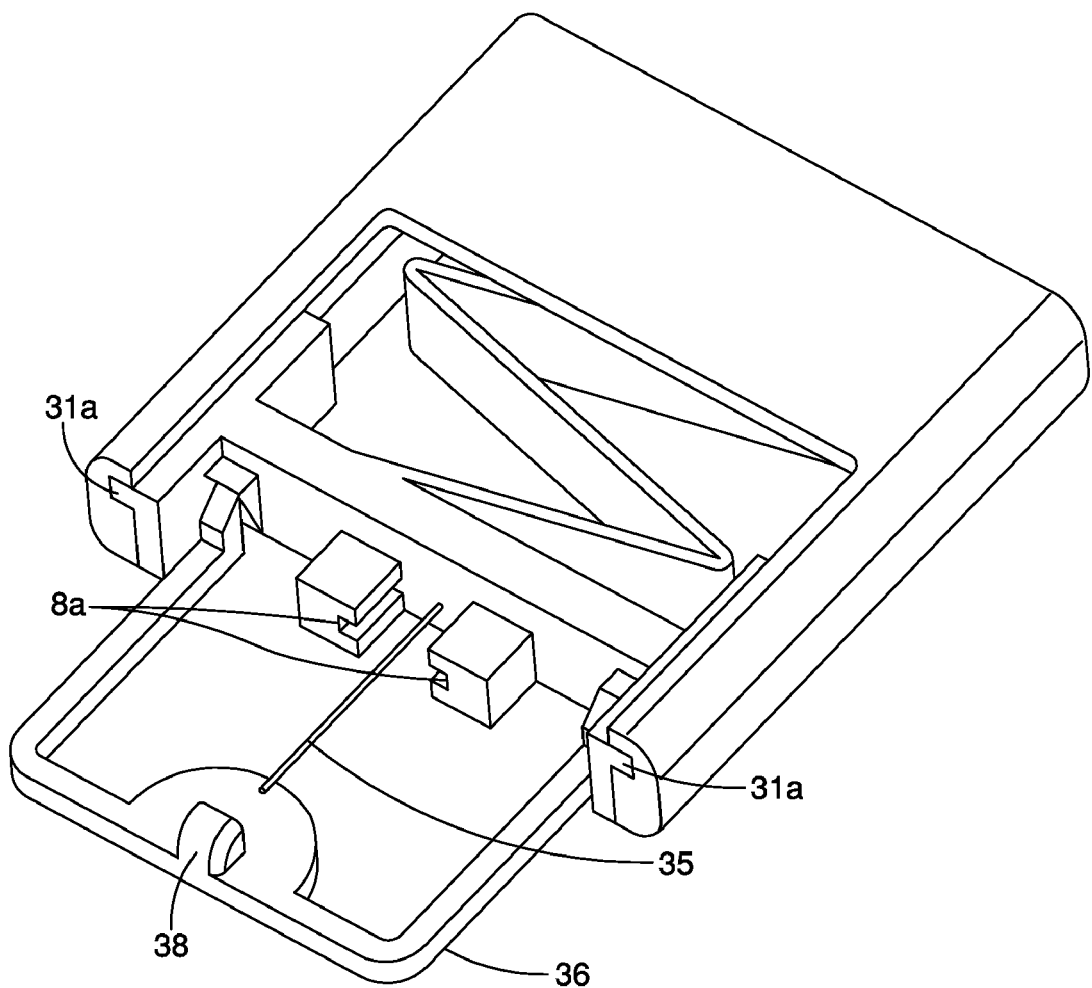
FIG. 9 shows the first embodiment of the injector device where the pivoting member is embracing the needle after insertion.

FIG. 6-11 shows a first embodiment of an injector device (29) which can be used for injection of the infusion part (0B) of the infusion set. In FIG. 6 the injector device is separated from the infusion part (0B) and FIGS. 7 and 8 show the same injector device (29) joined with an infusion part (0B). The injector device comprises a housing (30) with two longitudinally extending guiding means (31) formed as grooves in this embodiment and a longitudinally slidable member (32) having guiding means (31a), in this embodiment a rim, corresponding to the guiding means (31). A penetrating needle (35) is extending from the front part of the slidable member (32), and the needle (35) is at the end where it is fastened to the slidable member (32) surrounded by guiding means corresponding to the guiding means (13) on the infusion part (0B). The slidable member (32) is capable of moving from a retracted position to a forward position, and is driven from the retracted position to the forward position by a spring (34). The spring is located between the slidable member (32) and the back (33) of the housing. Optionally there is a spring support (37) (FIG. 8) which fits with the back of the housing thereby minimizing the risk of a malfunctioning spring. The injector device further comprises locking means (38) for maintaining the spring in a compressed state and release means (39) for disengaging the locking means. When the locking means (38) are disengaged, the spring (34) drives the slidable member (32) to its forward position, thus introducing the cannula positioned at the front end of the infusion part (0B) into the patient by means of the needle (35). After the introduction of the cannula, the injector device including the insertion needle (35) is withdrawn from the infusion part (0B) leaving the insertion needle in an exposed position. The pivoting member (36) can then be swung into a position where it embraces the needle (35) as shown in FIG. 9.

Figure 10:
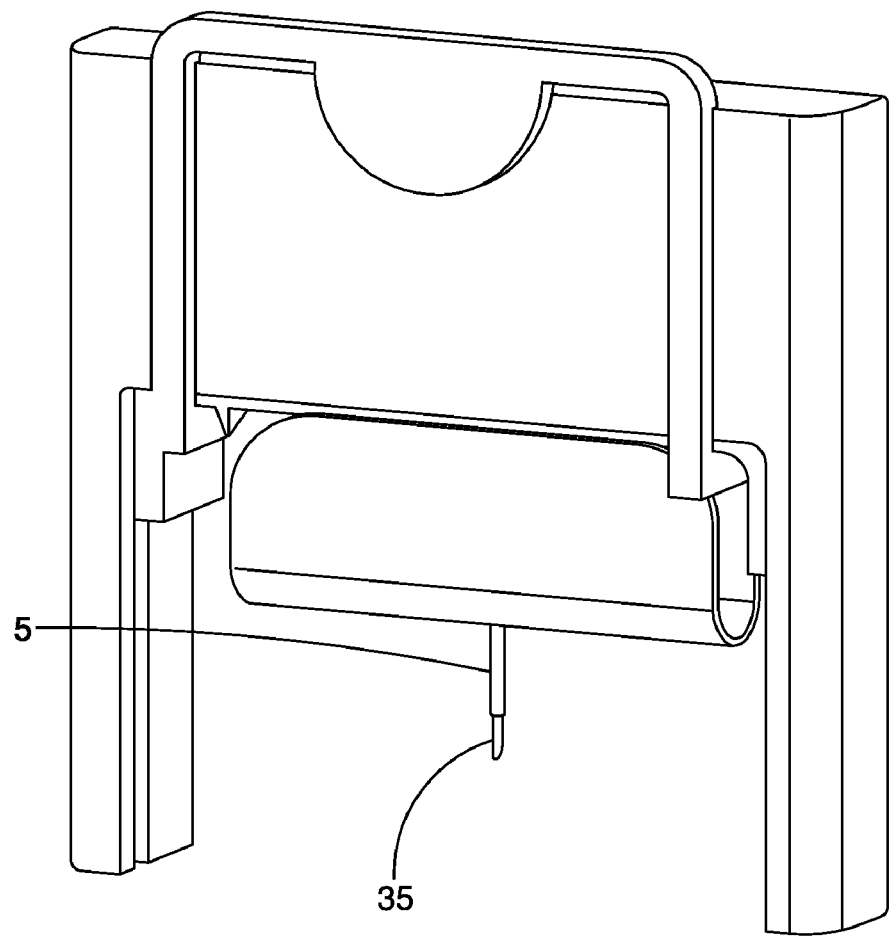
FIG. 10 shows the first embodiment of the injector device in the loaded and secured position before insertion.
Figure 11:
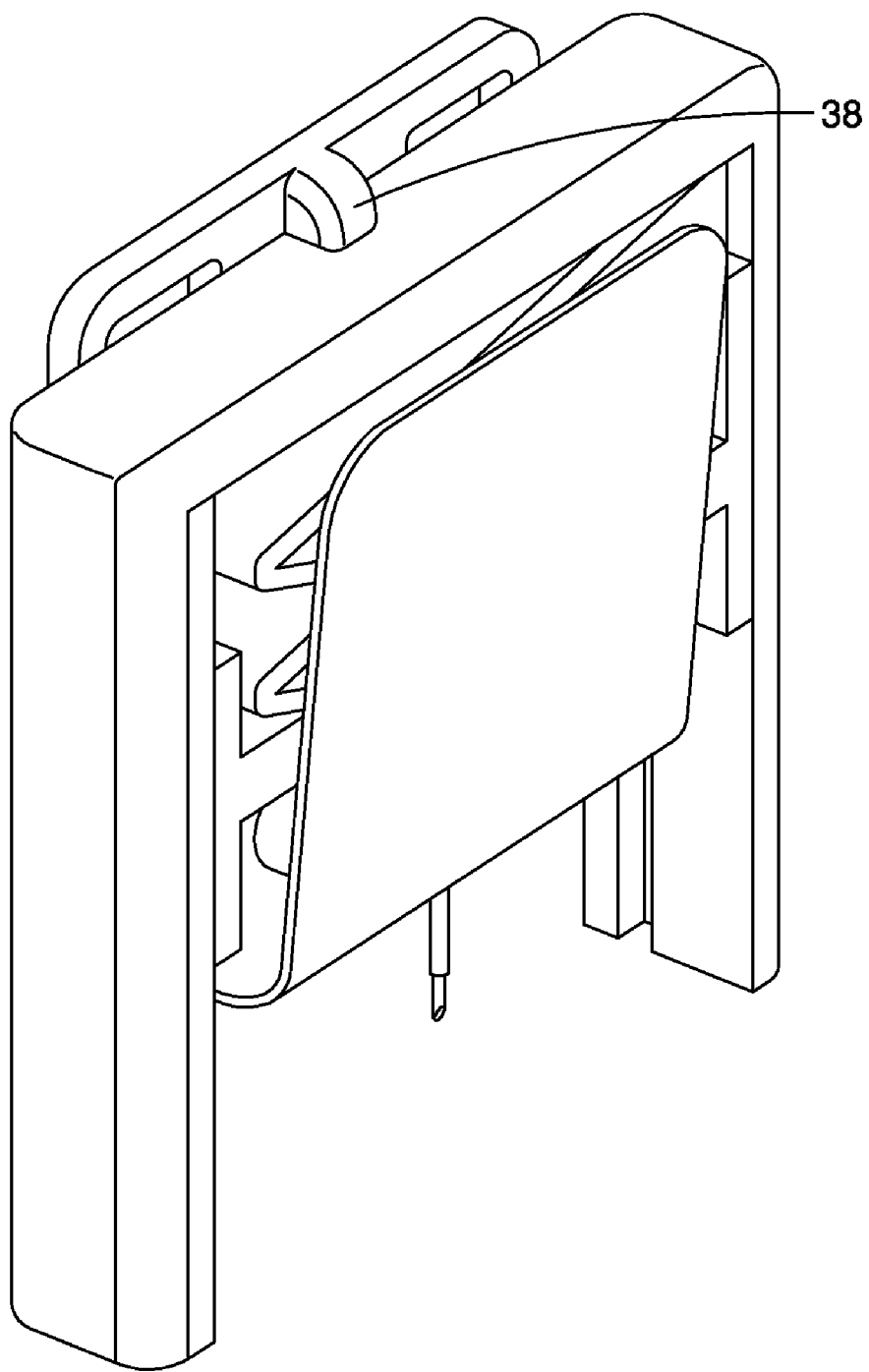
FIG. 11 shows the first embodiment of the injector device in the loaded and secured position before insertion from a second angle.

FIG. 10 and FIG. 11 show the same embodiment of the injector device in a loaded and secured position. Part of the pivoting member (36) acts as locking means (38). In FIG. 10 it can be seen how the needle (35) fits into the cannula (5) of the infusion part. The needle (35) will bring the cannula (5) with it during the skin penetration. After penetrating the skin the needle (35) secured to the injector will be withdrawn leaving the cannula inserted in the patient. In FIG. 11 the locking means are shown said locking means are disengaged when the tab (38) is pushed over the edge of the outer side of the back (33) of the housing.

Figure 12:
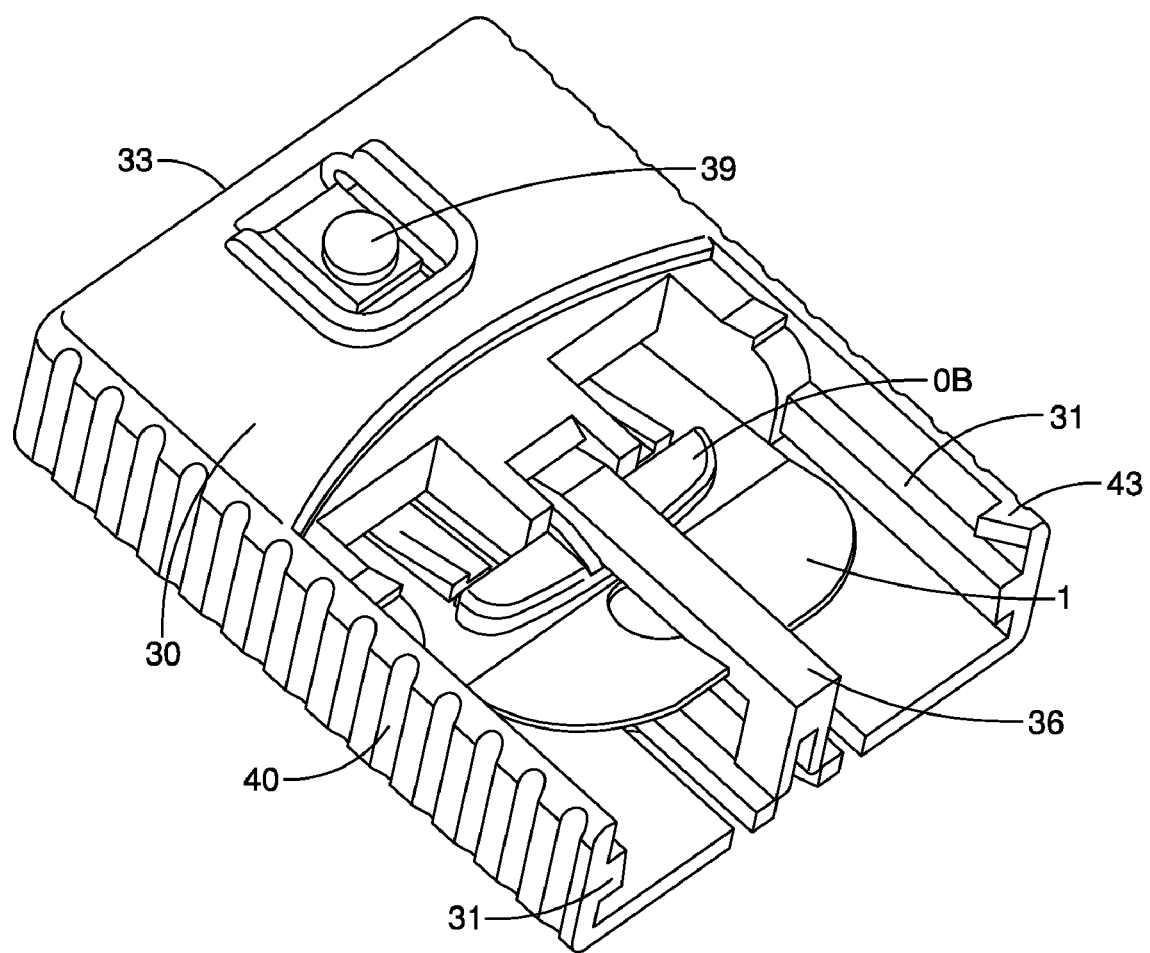
FIG. 12 shows a second embodiment of the injector device in a loaded and secured state before insertion.

FIGS. 12 to 17 show a second embodiment of the injector device according to the invention where the pivoting member (36) is fastened centrally in relation to the slidable member (32). FIG. 12 shows the injector device in a state where the pivoting member (36) protects the needle prior to injection of the cannula (5) of the infusion part (0B). The figure shows the housing (30) with another type of longitudinally extending guiding means (31), in this case a bar. The housing further has gripping means (40), preferably in the form of recesses, as means for getting a better grip of the injector device.

Centrally positioned release means (39) is shown on one of the main faces of the injector device. The advantage of a one button release mechanism is that the risk of a slanting injection reduced.

Figure 13:
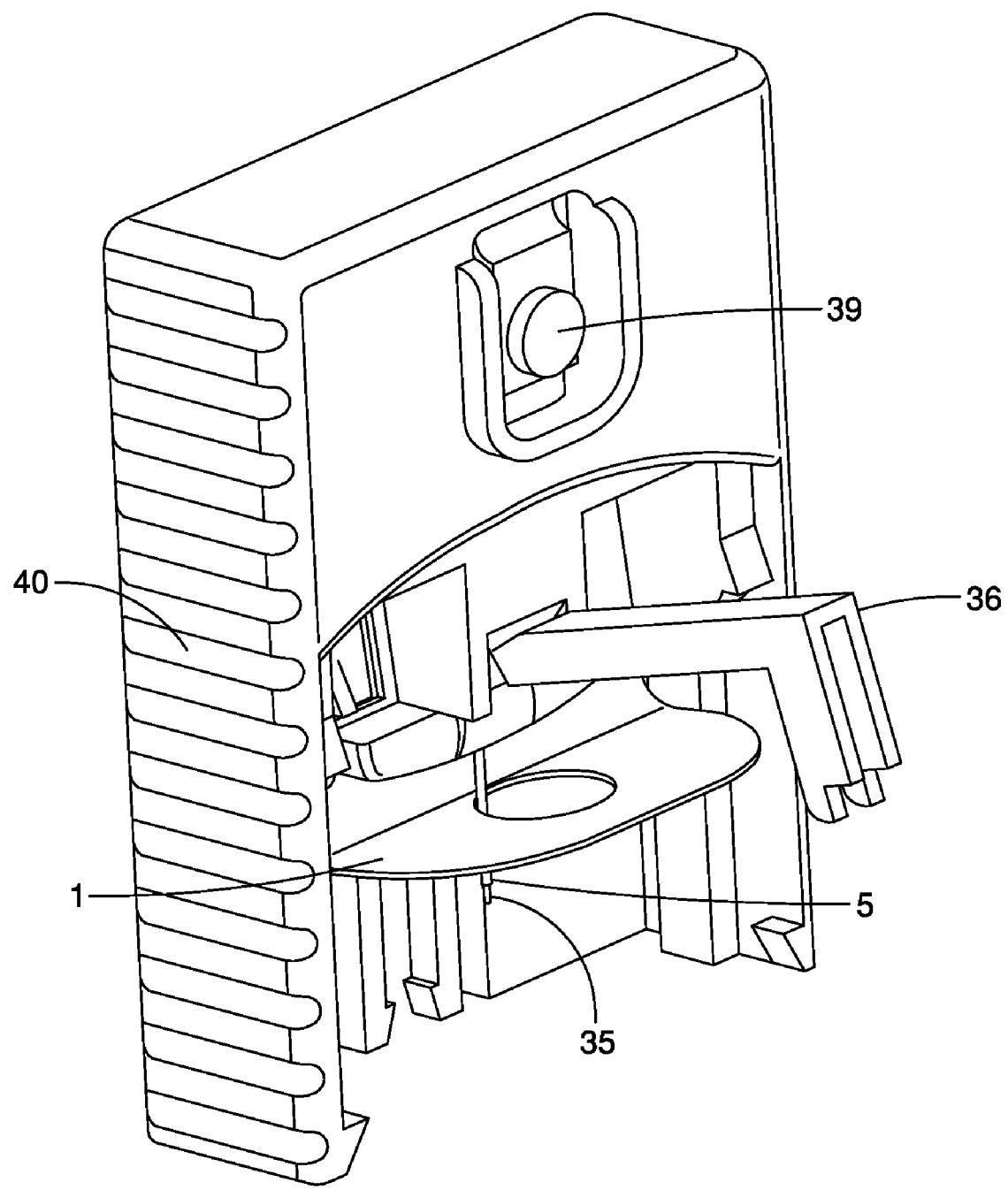
FIG. 13 shows the second embodiment of the injector device in a ready to use state.
Figure 14:
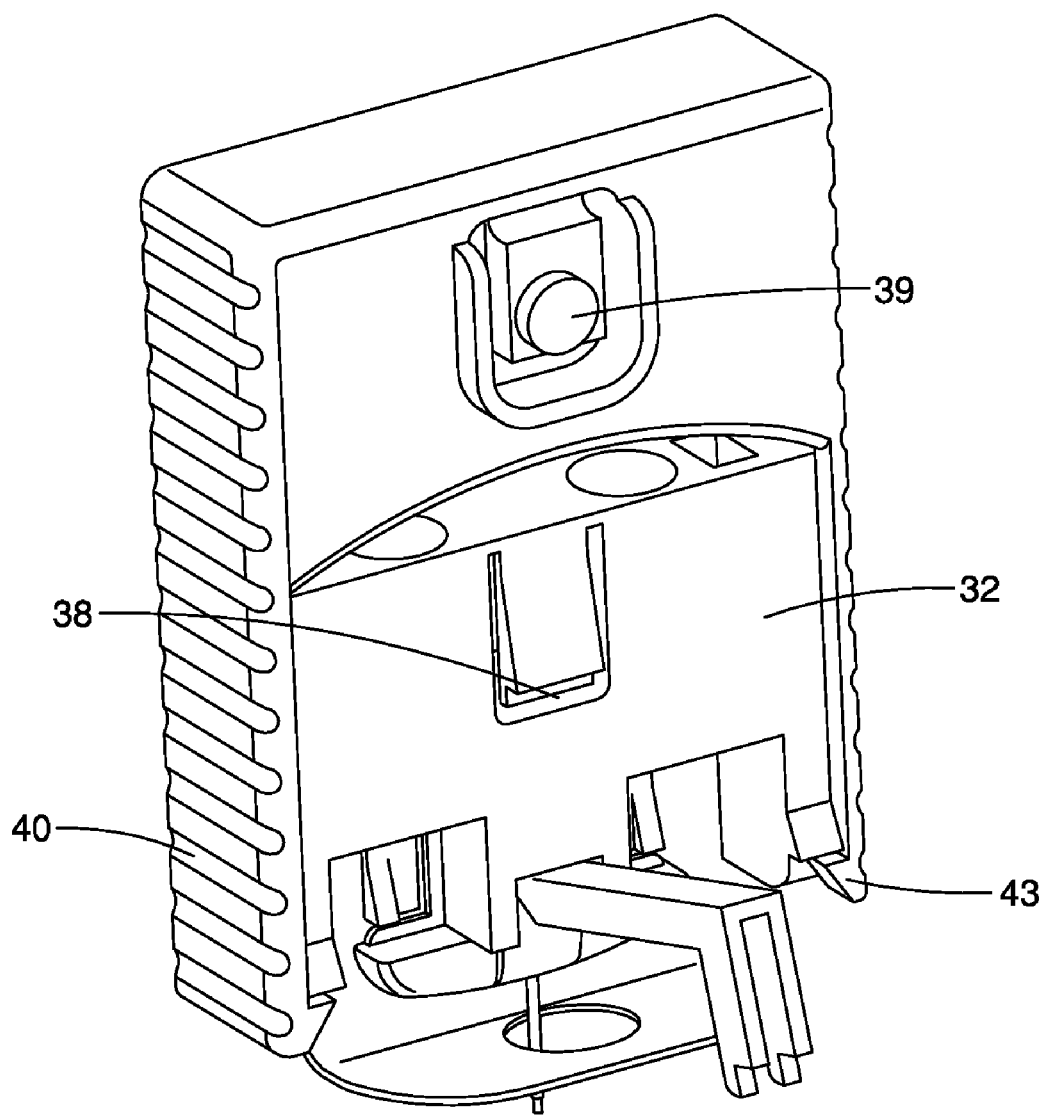
FIG. 14 shows the second embodiment of the injector device after insertion of the needle and before removing the injector from the infusion part.
Figure 16:
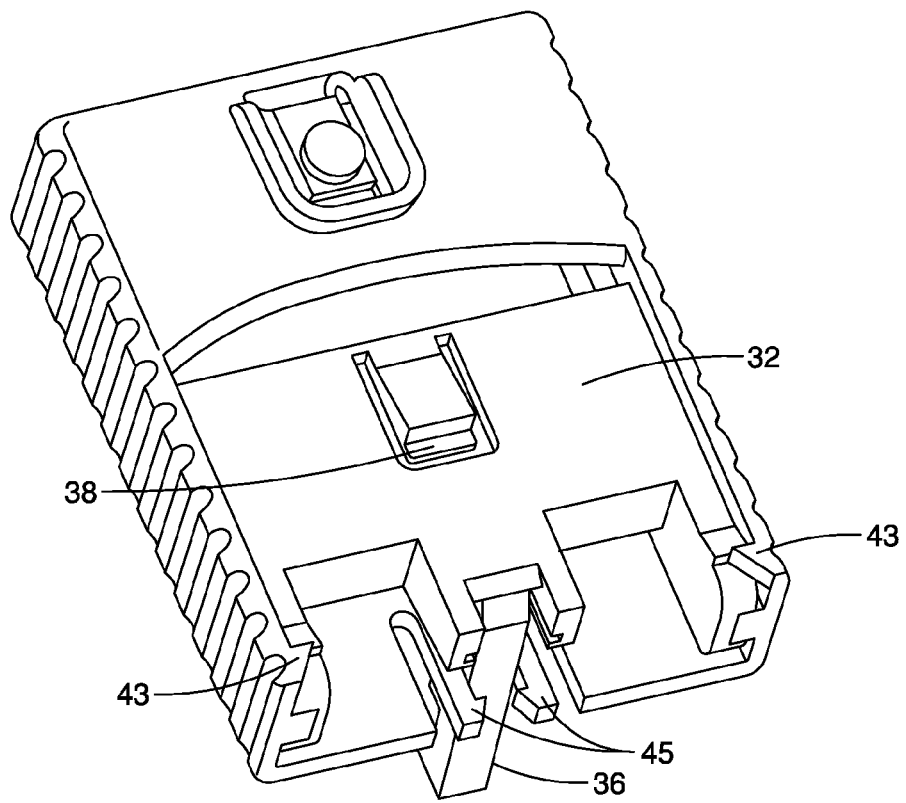
FIG. 16 shows the second embodiment of the injector device after the pivoting arm has been positioned to embrace the used needle.
Figure 17:
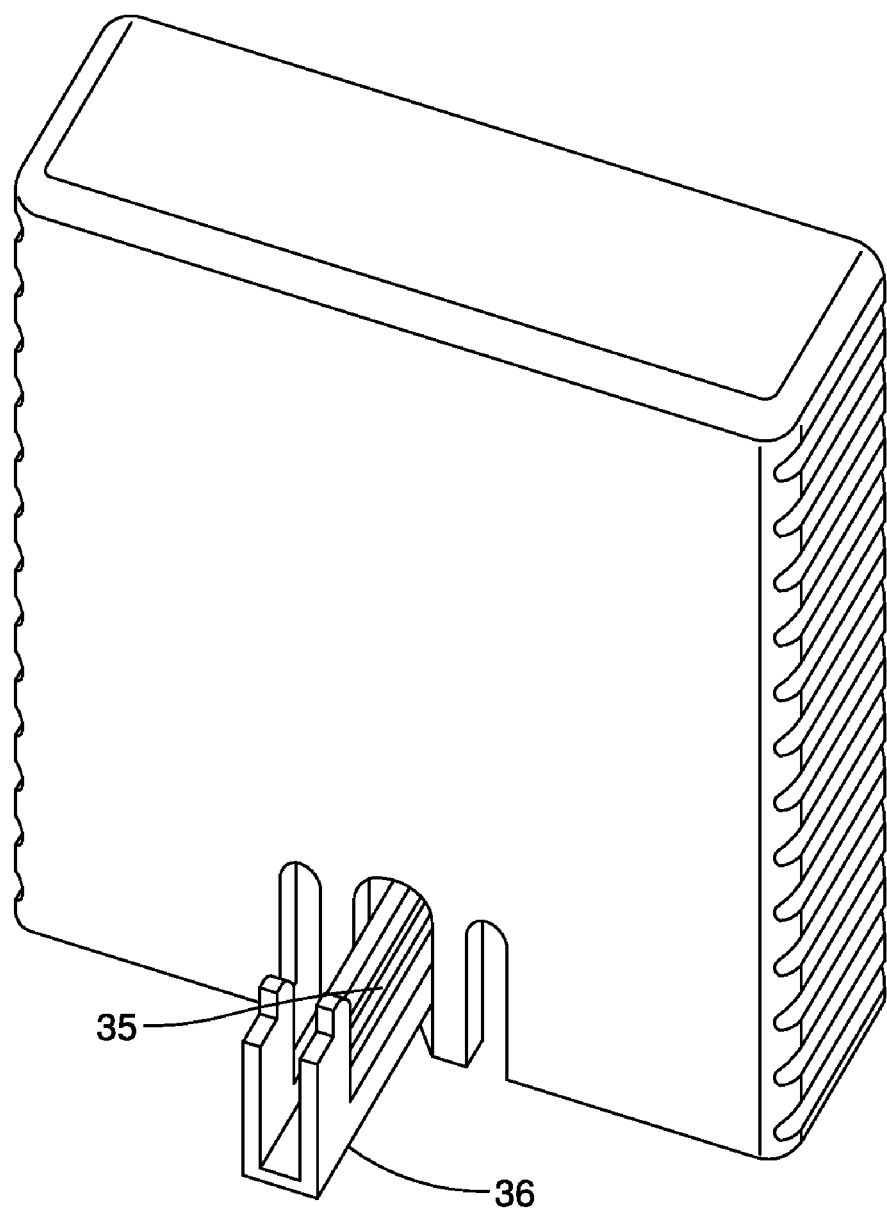
FIG. 17 shows the second embodiment of the injector device after the pivoting arm has been positioned to embrace the needle seen from another angle.
Figure 18:
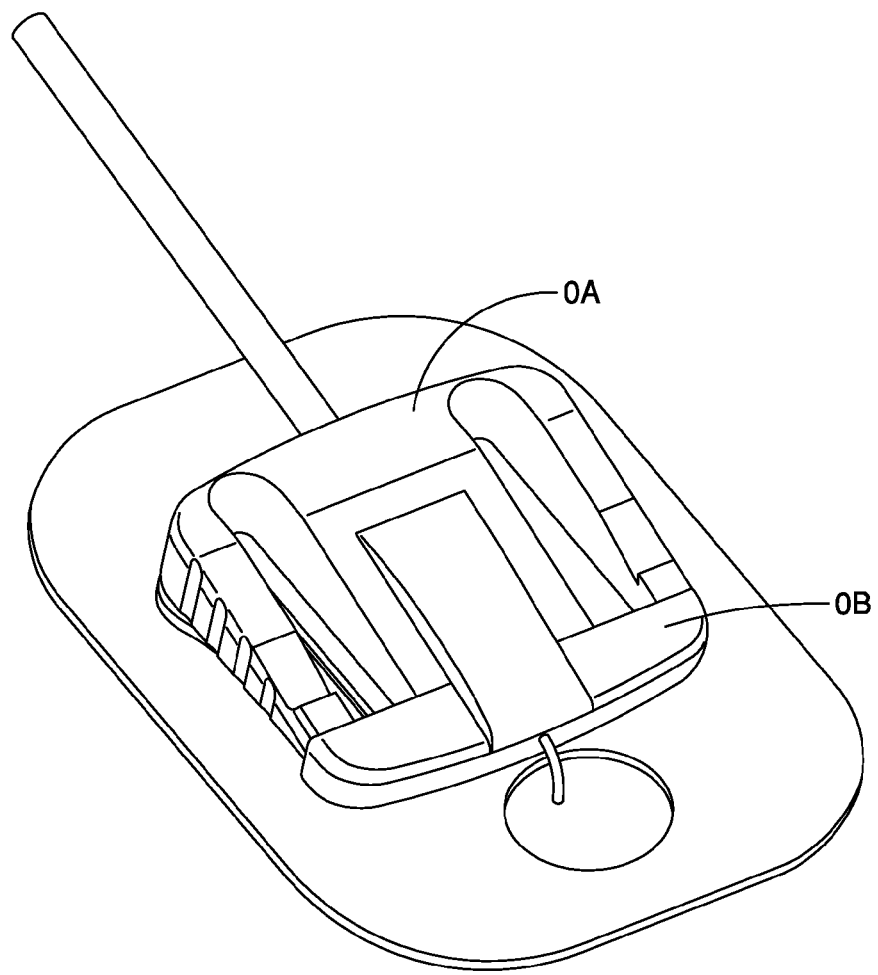
FIG. 18 shows an infusion set placed on the skin.

In FIG. 13 is shown an injector device prepared for insertion of the needle. The pivoting member is positioned away from the embracing position in an angle v≈90° in relation to the main axis of the injector device where the main axis is coincident with the insertion needle. The adhesive support (1) is positioned in such manner that the cannula (5) of the infusion part (0B) and the therein positioned needle (35) penetrates the adhesive support through an opening in the release liner. When the pivoting member is positioned essentially perpendicular to the main plane of the injector device it can provide a helping mean for achieving essentially vertical injection of the needle. Further FIG. 13 shows the needle (35) of the injector device inside the cannula (5). In FIG. 14 the injector device is in a released state where the needle (35) would have penetrated the skin. The housing in the embodiment of FIG. 14 has a stopping tab (43) corresponding to a protrusion on the slidable member that keeps the slidable member (32) within the housing (30) thereby making it easier to withdraw the needle since there is no risk that the slidable member slides out of the housing. In FIG. 15 the injector device has been withdrawn, leaving the cannula (5) of the infusion part (0B) inserted in the patient. In FIGS. 16 and 17 the pivoting member (36) is in a position where it embraces the needle (35) thereby protecting the surroundings from coming into contact with the used needle (35). In FIG. 18 the infusion part (0B) has been brought from the essentially vertical insertion position to a position essentially parallel to the skin.

Figure 19:
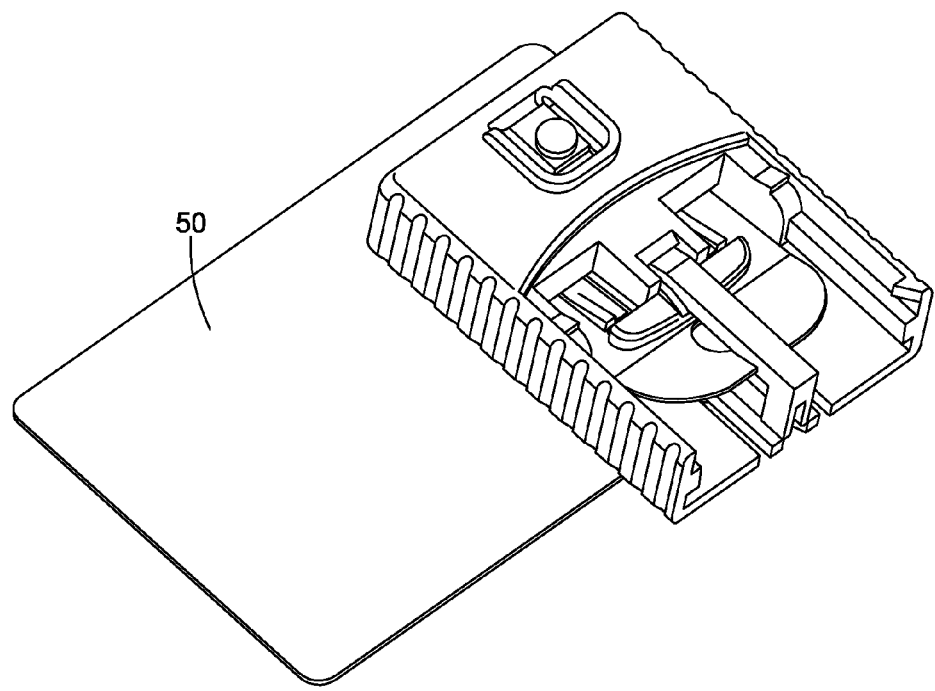
FIG. 19 shows the second embodiment of the injector device together with a credit card.

FIG. 19 shows the injector device together with a credit card to illustrate the size of the injector device.

Figure 20:
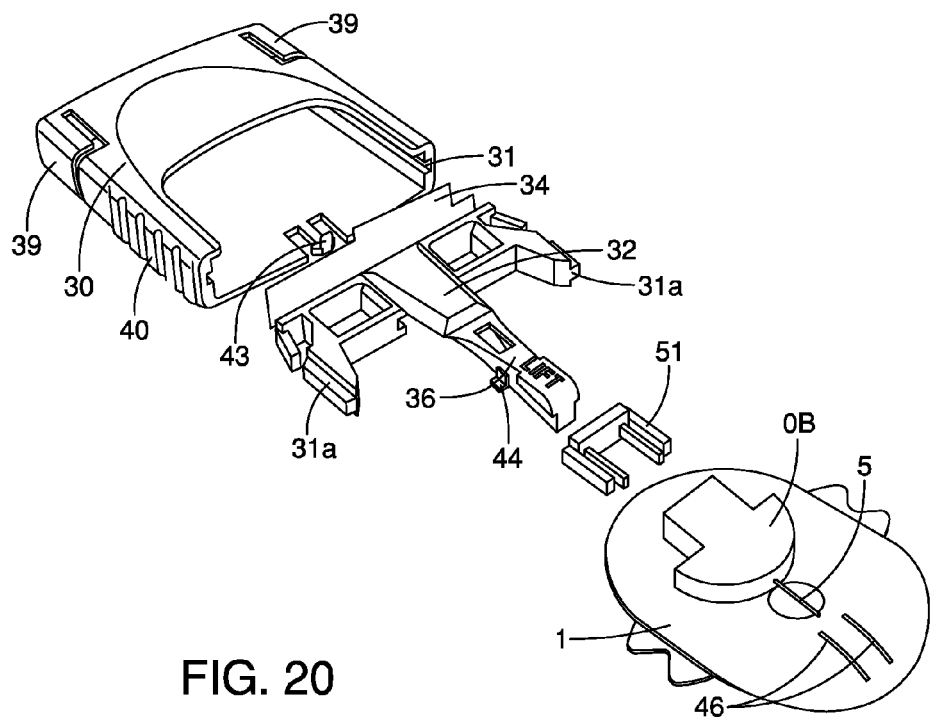
FIG. 20 shows a third embodiment of the injector device.

In FIG. 20 is shown a third embodiment of the injector device together with an infusion part (0B). This embodiment also has a housing (30) with longitudinally extending guiding means (31) and a longitudinally slidable member (32) of a different construction compared to the two first embodiments. Also the pivoting arm (36) and the spring (34) can be seen in this figure. In this embodiment the stopping tab (43) is placed centrally and has the form of a protrusion raising form the lower side of the housing (30). The release means (39) comprises two buttons placed on each side of the housing (30).

In FIG. 21 A-D it is shown how the infusion part (0B) along with the slidable member (32) and the spring (34) of the third embodiment fit into the housing (30). The unit (?) shown between the pivoting arm (36) and the insertion part (0B) is an adapter which makes it possible to use a standard injector for different guiding means (13) on the infusion part (0B).

In FIG. 22 A-B is shown fixing means (44) placed on the pivoting member (36). It is possible to temporarily attach a part of the adhesive support (1) to the fixing means in order to secure the position of the adhesive support in such a way that the adhesive surface of the support (1) will be turned towards the skin of the patient. Further release means (39) in the form of two buttons, one on each side of the housing (30), can be seen as well as the protruding stopping tab (43).

FIG. 23 A-B shows in further details and without the housing how the adhesive support (1) is hooked to the fixing means (44) due to at least one cutting (46) in the adhesive support (1).

FIG. 24 A shows the third embodiment of the injector device with an infusion part after insertion and 24 B shows the injector device after insertion and after the injector device has been removed from the insertion part (0B).

In FIG. 25 the pivoting member (36) of the injector device is in a position embracing the needle. A locking tab (45) fixes the pivoting arm in this position. This makes certain that the needle stays embraced by the pivoting arm and thereby minimizes the risk of somebody getting hurt by the needle.

In FIG. 26 A-D the cycle of use for the injector device is illustrated:

When the infusion set is delivered to the patient together with the injector device, the infusion part (0B) and the connector (0A) are packed separately and under sterile conditions, and the infusion part (0B) is placed in the injector device (FIG. 26 A). When the user wants to insert the infusion part (0B), the user pulls the pivoting arm and turns the arm perpendicularly to the housing (30) (FIG. 26 B). In this position the needle (35) placed on the slidable member (32) is exposed and the adhesive support is bend backwards with the adhesive surface turned towards the users skin. The user then pushes the buttons (39) on each side of the housing which releases the spring and pushes the slidable member (32) towards the user's skin (FIG. 26 C). The needle (35) will in this position penetrate the skin and place the cannula of the infusion part (0B) subcutaneous. After placing the infusion part (0B) the injector device is removed, and in order to protect the surroundings from the used needle (35) the pivoting arm (36) is turned approximately 180° to an angle w≈90° perpendicular to the main axis of the injector device, where it embraces the needle and make it safer to dispose of the device.

FIGS. 35A-E and 36A-E illustrates the cycle of use of the injector device seen respectively from the upper (FIG. 35) and the lower (FIG. 36) side of the injector device.

In FIGS. 35A and 36A the device is in a first state, which is the state the device would normally be delivered to the patient in, under sterile conditions. In this state the pivoting arm (36) is in a position where it embraces the needle (35) and the angle v between the main plane of the injector device and the pivoting arm is approximately 0°, if the release means (39) should unintentionally be pressed in this situation two protruding tabs (48) will prevent the slidable member (32) from being pushed forward.

In FIGS. 35B and 36B the device is prepared for use by lifting the pivoting arm (36) backwards thereby exposing the insertion needle (35) and also in this embodiment lifting the part of the release liner (41) which is attached to the pivoting arm (36), exposing the underlying adhesive support (1). In this position the pivoting arm (36) allows for insertion of the needle and is in an angle v to main plane of the injector device where 90°≦v≦180°, and in this position the injector device would be placed against the patient's skin.

In FIGS. 35C and 36C the release means (39) has been pressed and has released the spring (34). The spring has pushed the slidable member (32) forward until the slidable member was stopped by two stopping tabs (43). In this position the insertion needle (35) has penetrated the patient's skin and a part (this part covers an area around the needle in the full breadth of the adhesive support) of the adhesive surface of the adhesive support (1) is in contact with the patient's skin. In FIG. 36C it is shown how the second part (42) of the release liner is attached to the housing (30) and still covers the adhesive surface when the slidable member (32) is pushed forward.

In FIGS. 35D and 36D it is shown what happens when the injector device is removed from the patient, leaving the infusion part (0B) inserted subcutaneously. The user frees the first part (41) of the release liner from the pivoting arm (36) and then when pulling the injector device away the second part (42) of the release liner is also pulled away, exposing the adhesive surface of the adhesive support (1) and making it possible for the user to press the adhesive support towards the skin and thereby securing the infusion part (0B).

Finally after withdrawal of the insertion needle which in this embodiment is attached to the slidable member (32) in the injector device, it is shown in FIGS. 35E and 36E how the pivoting member (36) is placed in a position where it is embracing the needle thereby protecting the surroundings from getting stung. In order to get into this position the pivoting arm (36) is turned approximately 180° from the position in FIGS. 35D and 36D, and the angle w between the main plane of the injector device and the pivoting arm (36) is approximately 90°.

The invention claimed is:

1. An injector device for the subcutaneous introduction of a cannula of an infusion part into the skin of a patient, said device comprising:
   a housing including a back and longitudinally extending guiding means;
   a slidable member longitudinally slidable within the housing;
   an insertion needle unreleasably fastened to and moving together with the slidable member;
   a spring located between the back of the housing and the longitudinally slidable member;
   first locking means for maintaining the spring in a compressed state;
   release means for disengaging the locking means; and
   a pivoting member fastened to and moving together with the slidable member, the pivoting member being pivotable from a position in which the pivoting member allows for insertion of the needle into a position in which the pivoting member embraces the needle; wherein the pivoting member can embrace the needle when the slidable member is in a forward position and the spring is in a released state.

2. An injector device according to claim 1, wherein the pivoting member is placed approximately parallel to the housing when the pivoting member is in the position for embracing the needle.

3. An injector device according to claim 1, wherein the pivoting member is oriented at a second angle with respect to the housing of between about 0° and about 180° when the pivoting member is in the position for embracing the needle.

4. An injector device according to claim 1, wherein the slidable member comprises a lattice structure.

5. An injector device according to claim 1, wherein the release means comprises two positions placed on opposite sides of the housing.

6. The injector device of claim 1, wherein the pivoting member can embrace the needle when the slidable member is in a retracted position and the spring is in a tightened state.

7. An injector device for inserting a portion of a cannula of a medical device into the skin of a patient, the device comprising:
   a housing having a first end extending between a pair of arms;
   a slidable member at least partially received in the housing and being longitudinally slidable within the housing;
   an insertion member unreleasably connected to the slidable member, the insertion member being adapted for insertion of the cannula into the skin of the patient; and
   a pivoting member operably connected to the slidable member, the pivoting member being pivotable from an insertion position wherein the insertion member is insertable into the skin of the patient and a covering position wherein the insertion member is at least partially covered by the pivoting member; wherein the pivoting member can embrace the needle when the slidable member is in a forward position and the spring is in a released state.

8. The injection device of claim 7, further comprising a biasing member for biasing the slidable member with respect to the housing.

9. The injection device of claim 8, further comprising a first locking member for releasably maintaining the biasing member in a compressed state.

* * * * *